(12) United States Patent
Dubi et al.

(10) Patent No.: US 8,382,653 B2
(45) Date of Patent: Feb. 26, 2013

(54) METHOD AND SYSTEM FOR IMPROVING DIASTOLIC FUNCTION OF THE HEART

(75) Inventors: Shay Dubi, Tel-Aviv (IL); Igor Kovalsky, Givatayim (IL); Yair Feld, Haifa (IL); Amir Loshakove, Moshav Bazra (IL); Boaz Nishri, Kibbutz Maagan Michael (IL); Amit Tubishevitz, Tel-Aviv (IL)

(73) Assignee: Corassist Cardiovascular Ltd., Herliya Pituach (IL)

( * ) Notice: Subject to any disclaimer, the term of this patent is extended or adjusted under 35 U.S.C. 154(b) by 524 days.

(21) Appl. No.: 12/311,222

(22) PCT Filed: Sep. 25, 2007

(86) PCT No.: PCT/IL2007/001180
§ 371 (c)(1),
(2), (4) Date: Sep. 11, 2009

(87) PCT Pub. No.: WO2008/038276
PCT Pub. Date: Apr. 3, 2008

(65) Prior Publication Data
US 2010/0022821 A1   Jan. 28, 2010

Related U.S. Application Data

(60) Provisional application No. 60/846,748, filed on Sep. 25, 2006.

(51) Int. Cl.
*A61F 2/00* (2006.01)
*A61F 13/00* (2006.01)

(52) U.S. Cl. ............... 600/37; 600/16; 600/18; 267/69; 267/154; 267/166; 267/182; 5/652

(58) Field of Classification Search ............ 600/37, 600/16, 18; 267/69, 80–112, 154–157, 166, 267/170, 174, 179, 182; 5/652
See application file for complete search history.

(56) References Cited

U.S. PATENT DOCUMENTS

| | | | |
|---|---|---|---|
| 3,508,332 A | 4/1970 | Armstrong | |
| 3,618,214 A | 11/1971 | Armstrong | |
| 5,363,522 A * | 11/1994 | McGraw | 5/717 |
| 6,595,912 B2 | 7/2003 | Lau et al. | |
| 2001/0025171 A1 * | 9/2001 | Mortier et al. | 606/1 |
| 2002/0045800 A1 | 4/2002 | Lau et al. | |
| 2002/0188170 A1 * | 12/2002 | Santamore et al. | 600/37 |
| 2003/0032979 A1 * | 2/2003 | Mortier et al. | 606/213 |
| 2004/0002626 A1 | 1/2004 | Feld et al. | |
| 2004/0116992 A1 * | 6/2004 | Wardle et al. | 607/116 |

(Continued)

FOREIGN PATENT DOCUMENTS

| | | |
|---|---|---|
| WO | 03/007778 | 1/2003 |
| WO | 2004/066805 | 8/2004 |

(Continued)

*Primary Examiner* — John Lacyk
*Assistant Examiner* — Sunita Reddy
(74) *Attorney, Agent, or Firm* — Nixon & Vanderhye P.C.

(57) ABSTRACT

The present invention provides a system for improving diastolic function of the heart comprising elastic elements and attachment elements, wherein said elastic elements and said attachment elements are configured such that they are capable of being interconnected to form a chain formed of an alternating series of said elastic elements and said attachment elements, and wherein said attachment elements are adapted to be anchored in the wall of the heart and with option for drug delivery to the wall of the heart. The invention further provides devices, methods and kits, for mounting the ventricular function assisting device of the invention.

33 Claims, 11 Drawing Sheets

U.S. PATENT DOCUMENTS

| | | |
|---|---|---|
| 2004/0153101 A1 | 8/2004 | Bolduc et al. |
| 2004/0267279 A1 | 12/2004 | Casutt et al. |
| 2006/0161040 A1 | 7/2006 | McCarthy et al. |
| 2006/0199995 A1 | 9/2006 | Vijay |

FOREIGN PATENT DOCUMENTS

| | | |
|---|---|---|
| WO | 2005/041745 | 5/2005 |
| WO | 2006/033107 | 3/2006 |

* cited by examiner

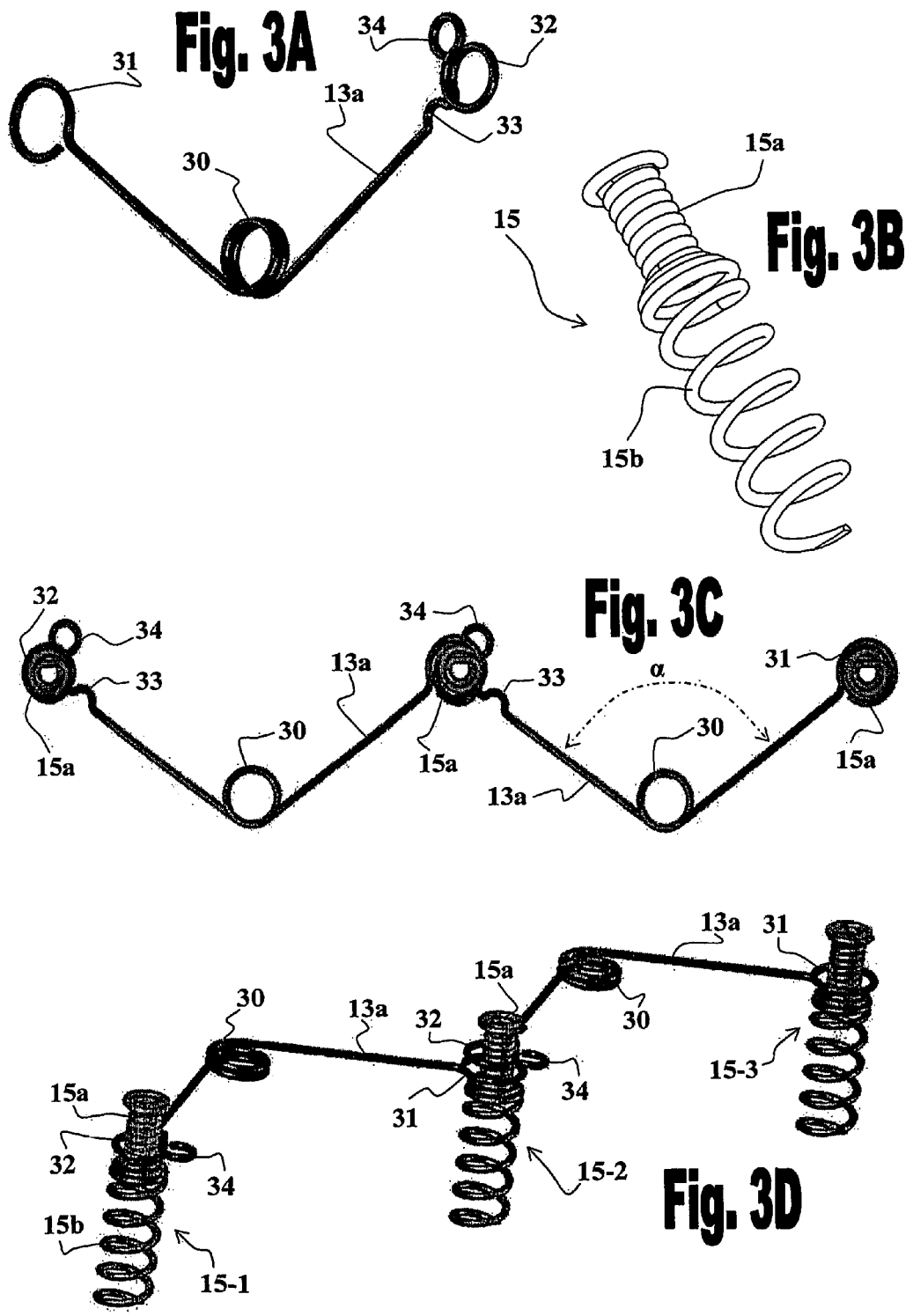

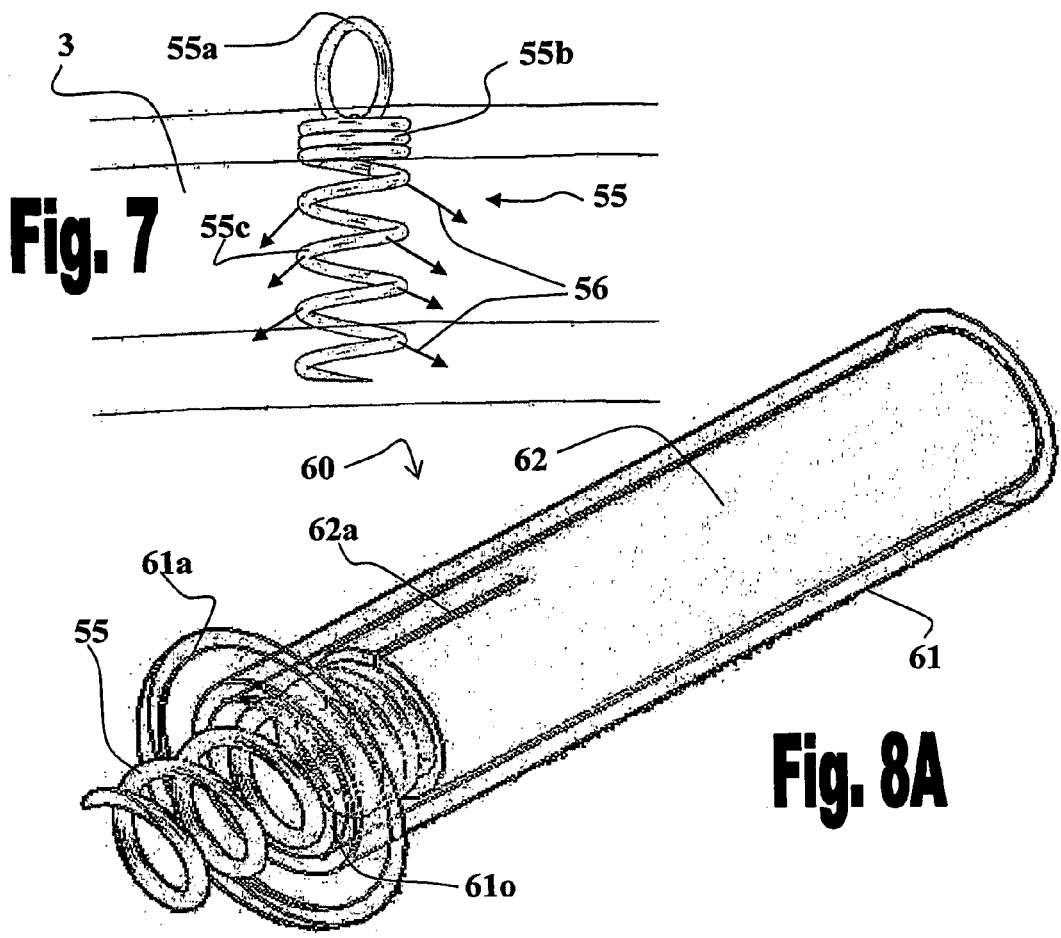
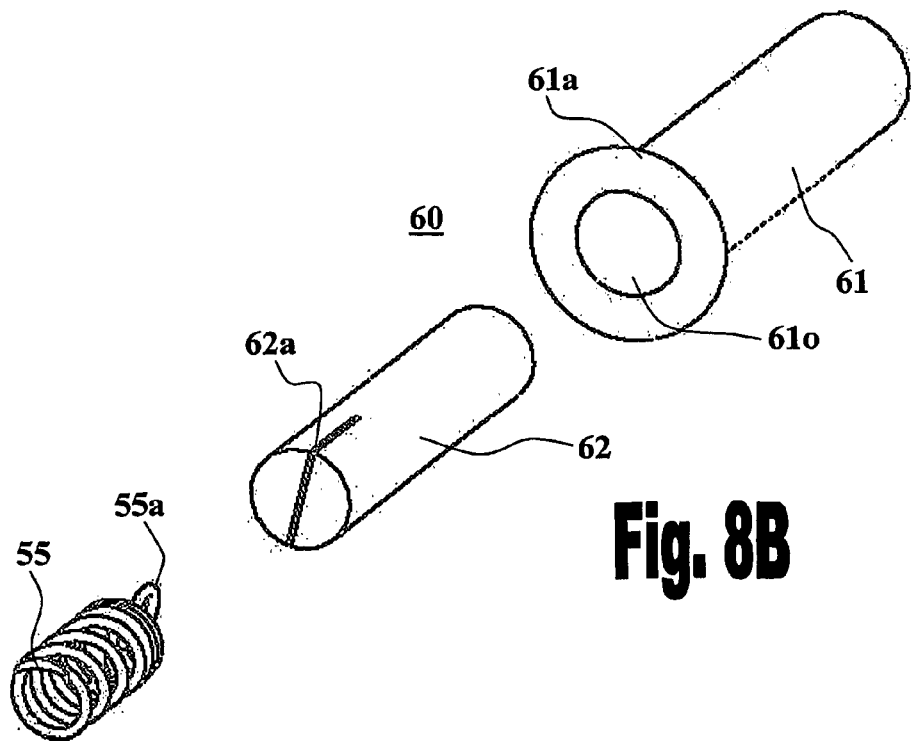

METHOD AND SYSTEM FOR IMPROVING DIASTOLIC FUNCTION OF THE HEART

This application is the U.S. national phase of International Application No. PCT/IL2007/001180, filed 25 Sep. 2007, which designated the U.S. and claims the benefit of U.S. Provisional Application No. 60/846,748, filed 25 Sep. 2006, the entire contents of each of which are hereby incorporated by reference.

FIELD OF THE INVENTION

The present invention relates to methods and devices for improving ventricular function of the heart and, more particularly, to in-vivo methods and devices for improving diastolic function of the left ventricle of the heart.

BACKGROUND OF THE INVENTION

Heart failure (HF) is a complex clinical syndrome that can result from any structural or functional cardiac disorder that impairs the ability of the ventricle to fill with or eject blood. The cardinal manifestations of HF are dyspnea and fatigue, which may limit exercise tolerance, and fluid retention, which may lead to pulmonary congestion and peripheral edema. Heart failure is most commonly associated with impaired left ventricle (LV) systolic function. A widely used index for quantifying systolic function is 'ejection fraction' (EF), defined as the ratio of stroke volume to end-diastolic volume, which can be estimated using techniques such as radiocontrast, radionuclide angiography, and/or echocardiography. The normal value of EF is 0.67±0.08, which is frequently depressed in systolic heart failure even when the stroke volume is normal. A value of EF≧0.50 is commonly used as an indicator of normal systolic function. It is notable, however, that as much as 30-50% of all patients with typical symptoms of congestive heart failure have a normal or slightly reduced ejection fraction, that is, a value of EF≧0.45.

The term diastolic heart failure (DHF) generally refers to the clinical syndrome of heart failure associated with preserved left ventricular ejection fraction, in the absence of major valvular disease.

Primary diastolic dysfunction is typically observed in patients with hypertension and hypertrophic or restrictive cardiomyopathy, but can also occur in a variety of other clinical disorders and has a particularly high prevalence in the elderly population. Aging is associated with 'physiologic' diastolic dysfunction due to the increase in LV muscle mass and changes in passive elastic properties of the myocardium, hence, the concern of an increase in the incidence of diastolic dysfunction as the aging of the western world population progresses.

To one of ordinary skill in the art, there is thus a need for, and it would be highly advantageous to have an in-vivo method and device for improving diastolic function of the left ventricle of the heart, while minimally disturbing systolic function of the heart. Moreover, there is a need for such a method and device which is biocompatible and is specially configured for compact and long-term reliable use in humans.

Various in-vivo methods and devices for improving diastolic function of the heart are described in International patent applications Nos. PCT/IL02/00547, PCT/IL05/01014, PCT/IL04/00986, and PCT/IL04/00072, of the same assignee hereof, the descriptions of which is incorporated herein by reference. The aforementioned international patent applications describe elastic means used for improving diastolic function of the right or left ventricle of the heart by pushing and/or pulling, an inner and/or outer wall region of the ventricle during the cardiac cycle while minimally disturbing the heart function. The present invention provides modifications, improvements, accessories, and new methods and devices, for improving the diastolic function of the heart.

It is an object of the present invention to provide methods and devices for treating systolic and diastolic dysfunctions.

It is a further object of the present invention to provide accessories and a kit for mounting devices for treating systolic and diastolic dysfunctions of the outer surface of the wall of the heart.

It is another object of the present invention to provide improved configurations suitable for mounting ventricular assisting means on the wall of the heart.

Other objects and advantages of the invention will become apparent as the description proceeds.

SUMMARY OF THE INVENTION

The present invention is directed to a system, method, kit and devices for improving diastolic function of the heart comprising elastic elements configured to be mounted on the wall of the heart by means of attachment elements, said attachment elements are adapted to be threaded into, or anchored in, the wall of the heart, and to provide an anchor for curved fasteners formed at, or attached to, extremities of the elastic elements. The system preferably comprise one or more substantially parallel rows of elastic elements mounted on the wall of the heart by means of the attachment elements, wherein each pair of adjacent elastic elements are engaged in anchoring means of a mutual attachment element.

The term elastic element used herein to refer to an element capable of restoring its original shape after being deformed. The elastic elements of the invention may be prepared from conventional materials having known elasticity properties suitable to be used in the system and devices of the invention (e.g., Conichrome (FWM 1058)).

In one aspect the present invention is directed to a system for improving diastolic function of the heart comprising:
a) Elastic elements; and
b) Attachment elements;
   wherein said elastic elements and said attachment elements are configured such that they are capable of being interconnected to form a chain formed of an alternating series of said elastic elements and said attachment elements; and wherein said attachment elements are adapted to be anchored in the wall of the heart.

The elastic elements preferably comprise one or more torsion springs, each of which comprises two arms forming a "V" or "U" like shape. The extremities of the elastic elements are preferably bent to form curved fasteners capable of being engaged in anchoring means provided in the attachment elements.

In one specific embodiment of the invention the elastic elements comprise torsion springs and two arms forming a "V"-like shape, wherein each of the arms comprises a curved fastener. The curved fasteners may be shaped in a form of a spiral, or a "G"-like shape, capable of being engaged in anchoring loops provided in the attachment elements. The end portion of each arm may be curved into an "S"-like shape, wherein the bottom part of the "S"-like shape is further curved to provide the spiral, or a "G"-like shape curved fastener. This configuration may be advantageously employed for engaging the curved fasteners of adjacent elastic elements at opposing sides of an anchoring loop of an attachment element, such that opposing tangential mechanical forces applied by the adjacent elastic elements over the attachment element are substantially canceled. This configuration advantageously minimizes the wear between the attachment elements and the elastic elements, substantially facilitates the implantation procedure (by attaching the elastic element to the attachment element), and efficiently prevents unintended release of the elastic elements from the attachment elements.

Advantageously, each elastic element is comprised of a relatively straight arm and an arm having a curved section relative to the plane of the torsion spring and the relatively straight arm of the elastic element, thereby permitting the crossing of an arm having a curved section of a first elastic element with a relatively straight arm of an adjacent elastic element, while preventing physical contact therebetween.

Advantageously, at least one of the curved fasteners of the elastic elements may comprise one or more fastening loops capable of being placed and tightened over a portion of an anchoring element. In this case the other curved fastener may be provided in a form of an anchoring (closed or semi-closed) loop, such that adjacent elastic elements may be secured to an attachment element by placing the anchoring loop provided in one arm of one of the elastic elements over the anchoring means of the attachment element and thereafter securing it thereto by tightening the one or more fastening loops provided in an arm of the adjacent elastic elements thereupon, over the anchoring means of the attachment element. A widening loop may be provided on, or near, the fastening loops for assisting in widening the fastening loops before placing them over a portion of the anchoring element. A saddle may be formed on an arm section of the elastic element near the curved fasteners for assisting in widening the fastening loops by pulling the widening ring towards the saddle by means of forceps, pliers, or any other instrument suitable for this purpose.

In another specific embodiment of the invention the elastic elements are comprised of two "V"-shaped torsion springs having a mutual arm, which form a zigzagged shape element wherein the non-mutual arms are more or less perpendicular and wherein said non-mutual arms comprise curved fasteners configured such that the curved fasteners of two adjacent elastic elements engage opposing sides of an anchoring loop of an attachment element, thereby providing an assembly which substantially cancels opposing mechanical forces applied by adjacent elastic elements over a mutual attachment element.

The attachment elements may be formed in a shape of a helix having an attachment section and a head section, wherein the attachment section is adapted to be threaded into a tissue and the head section comprises the anchoring means. The attachment element may further comprise a neck section, provided between the attachment section and the head section, said neck section is adapted to prevent excess threading of the attachment element into the tissue. Preferably, the neck section is formed by abruptly reducing the distances between the helix loops above the attachment section of the attachment element.

The anchoring means of the attachment elements may be a continuation of the neck section wherein the radius of the helix loops is slightly reduced. Alternatively, the anchoring means are implemented as anchoring loops provided in the attachment element, wherein the plane of the anchoring loop is substantially parallel to, or coincides with, a concentric axis of the attachment element.

Alternatively, the attachment elements are a type of intramural anchor having one or more barbs attached to a nail section of the intramural anchor and configured to be introduced into the tissue and prevent departure of the attachment element after it is inserted into the tissue. More particularly, the barbs are pressed along portions of the nail section of the intramural anchor during insertion into the tissue, and thereafter their state is changed into an "open" state by slightly pulling the intramural anchor proximally such that the proximal sides of the barbs are moved radially away from the nail section, while the distal side of the barbs remain attached thereto. This attachment element preferably comprises anchoring means such as the anchoring loop which plane is substantially parallel to, or coincides with, a concentric axis of the attachment element. The attachment element may further comprise stoppers provided near the anchoring means and adapted to prevent excessive insertion thereof into the tissue, and to further prevent departure of the attachment element therefrom.

In another aspect, the present invention is directed to a device for improving diastolic function of the heart comprising an elastic element comprising one or more torsion springs, each of which comprising two arms forming a "V" or "U" like shape, wherein the extremities of said elastic element are bent to form curved fasteners capable of being engaged in an anchoring loop or ring.

The device of the present invention is different from the devices described in WO 2004/066805 by virtue of the curved fasteners formed at the extremities of the device. This feature is highly advantageous in that it permits the practitioner to connect a series of such devices in the form of chains or rows along the heart wall. In particular, the use of substantially parallel rows of the elements has been found to be particularly advantageous for: preventing restriction of the myocardium, enabling versatility and modularity of the implantation procedure, as well as in increasing the variability of the total force supplied to the myocardium (e.g. a structure of strong medial elastic elements and relatively weaker peripheral elastic elements).

The system may further comprise an elastic wire or stretchable cord capable of being connected to the attachment elements at the extremities of the chain formed of the alternating series of the elastic elements and the attachment elements, wherein said elastic wire or stretchable cord and said chain of elastic elements and attachment elements encircles a perimeter of the heart.

The system may further comprise an inflatable balloon capable of being introduced into a ventricle of the heart and being inflated thereinside, and/or one or more compressible elements adapted to be threaded into the wall of the heart.

In another aspect the invention is directed to a method for improving diastolic function of the heart, comprising:
  a) Performing a chest incision; (alternatively—mini-left thoracotomy or small incisions as in keyhole surgery approach)
  b) Attaching an attachment element to the wall of the heart, said attachment element is capable of puncturing the heart tissue and being advanced or threaded thereinto;
  c) Determining the distance from a previously attached attachment element to a location for a new such attachment element to be attached to the wall of the heart, preferably by means of a distance indicating instrument having one or more arms having suitable lengths;
  d) Attaching said new attachment element to the wall of the heart at said location;
  e) Attaching (either manually or optionally by using a gripping tool) an elastic element to anchoring means provided in said previously attached attachment elements and said new attachment element by means of attachment means provided in the extremities of said elastic element;

f) Repeating steps c) to e) to form a chain of an alternating series of said elastic elements and said attachment elements.

Conveniently, the attachment elements may be attached by means of a gripping tool, as follows:
- A) Gripping the anchoring means of an attachment element by said gripping tool;
- B) Puncturing the wall of the heart with a sharp tip of said attachment element and advancing/threading said attachment element thereinto until tissue resistance is encountered; and
- C) Removing said gripping tool.

The method may further comprise mounting additional one or more such chains of alternating series of elastic elements and attachment elements on the wall of the heart, as follows:
- i) Determining a distance from a previously installed chain of said elastic elements and said attachment elements, preferably by means of a distance indicating instrument having one or more arms having suitable lengths; and
- ii) Mounting an additional chain of alternating series of elastic elements and attachment elements on the wall of the heart within said distance, by carrying out steps b) to f) above.

Preferably, the one or more chains of alternating series of elastic elements and attachment elements are substantially parallel The method may further comprise attaching an elastic wire or stretchable cord to the attachment elements at the extremities of the chain formed of the alternating series of the elastic elements and the attachment elements, wherein said elastic wire or stretchable cord and said chain of elastic elements and attachment elements encircles a perimeter of the heart.

The method may further comprise introducing an inflatable balloon into a ventricle of the heart and inflating the same thereinside. Additionally or alternatively, the method may further comprise threading one or more compressible elements into the wall of the heart.

In yet another aspect the invention is directed to a kit of elements and instruments for mounting a ventricular function assisting system on the wall of a heart, comprising: one or more elastic elements capable of being attached to a wall of a heart, at least two attachment elements capable of being connected to anchoring means provided in said attachment elements, a gripping tool adapted to grip and hold said anchoring means, and one or more distance indicating instrument capable of being used to indicate distances between adjacent attachment elements and/or the distances between interconnected chains of said attachment and elastic elements.

The kit may further comprise one or more compressible elements capable of being threaded into the wall of the heart, expandable balloons capable of being introduced into a ventricle of the heart and inflated thereinside, and/or an elastic wire or stretchable cord capable of being connected to the anchoring means of said attachment elements.

BRIEF DESCRIPTION OF THE DRAWINGS

The present invention is illustrated by way of example in the figures of the accompanying drawings, in which like references indicate similar elements and in which:

FIGS. 3A and 3B schematically illustrate an embodiments of the attachment and elastic elements;

FIGS. 3C and 3D schematically illustrates the attachment of the elastic elements to the attachment elements shown in FIGS. 3A and 3B;

FIGS. 6A to 6C illustrate yet another preferred embodiment of the elastic element and of its connectivity to a respective attachment element, wherein FIG. 6A is an upper view of the elastic element, FIG. 6B is a perspective view of the attachment element, and FIG. 6C is a perspective view showing the connectivity of the elastic and attachment elements;

FIG. 7 schematically illustrates a preferred embodiment of the attachment elements comprising drug-containing coats;

FIGS. 8A and 8B respectively show perspective and exploded views of one preferred embodiment of a device for fastening attachment elements to the wall of the heart;

FIGS. 9A to 9D illustrate another preferred embodiment of a device for fastening attachment elements to the wall of the heart, wherein FIG. 9A is a perspective view of the device, FIGS. 9B and 9C are perspective views of inner parts of the device, and FIG. 9D is a perspective longitudinal section view of the device;

FIGS. 10A to 10C illustrate another preferred embodiment of a device for fastening attachment elements to the wall of the heart, wherein FIG. 10A is a perspective view of the device, FIG. 10B is a perspective longitudinal section view of the device, and FIG. 10C is a perspective view of inner shaft of the device;

FIGS. 11A to 11C illustrate another preferred embodiment of a device for fastening attachment elements to the wall of the heart, wherein FIG. 11A is a perspective view of the device, FIG. 11B is a perspective view showing inner parts of the device, and FIG. 11C is a longitudinal section view of a rotatable element of the device;

FIGS. 12A to 12F show perspective views of instruments for guiding the practitioner in determining suitable distances between adjacent attachment elements, and between rows of such elements on the wall of the heart, wherein FIGS. 12A and 12B illustrate an instrument which may be used for designating two different distances, FIG. 12C illustrates an instrument designed for designating a distance and a tolerable deviation, FIG. 12D illustrates another embodiment of the instrument shown in FIG. 12C which employs a ring for designating tolerable deviations, FIG. 12E illustrates an embodiment of the instrument comprising a closed frame for measuring distances and placing attachment elements, and FIG. 12F illustrates an embodiment of the instrument, which advantageously enables simple and accurate use and handling by the surgeon;

DETAILED DESCRIPTION OF PREFERRED EMBODIMENTS

The present invention provides various embodiments of ventricular function assisting devices designed for treating diastolic and/or systolic dysfunctions. The devices of the invention are designed to assist in the operation of the heart by aiding in reducing the pressures thereinside during systolic function, and aiding in increasing the pressure during diastolic function. The present invention further provides means for mounting a ventricular function assisting device of the invention on the wall of the heart of a treated subject.

Figure 1:
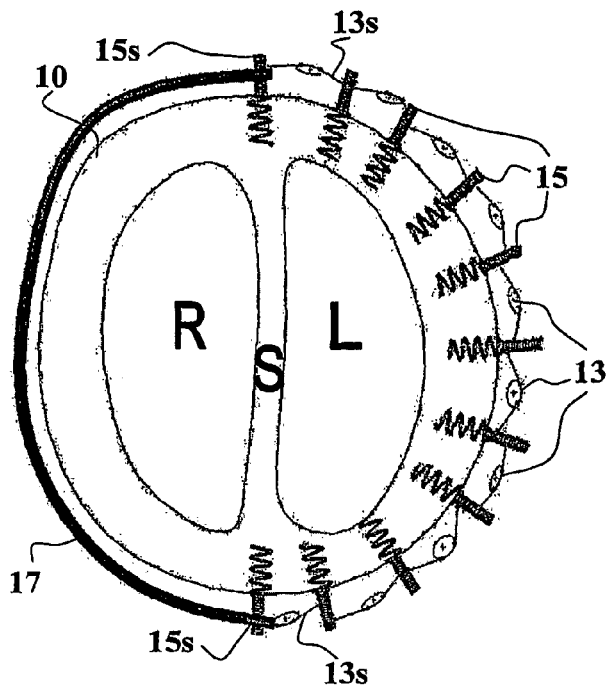
FIG. 1 schematically illustrates a preferred embodiment of the invention comprising a sequence of elastic elements arranged on the outer wall of the left ventricle and an elastic wire or stretchable cord mounted over the outer wall of the right ventricle.

FIG. 1 illustrates a preferred embodiment of the invention wherein a sequence of elastic elements 13 are mounted over the outer wall of the left ventricle (L), and an elastic wire or stretchable cord 17 is mounted over the outer wall of the right ventricle (R), of heart 10, by means of attachment elements 15. Elastic elements 13 preferably have a "U" or "V" like shape which arms include detachable means at their ends for detachably connecting them to the attachment elements 15. Attachment elements 15 may be attached on, or threaded into, the wall of the heart 10 in a lined sequence having suitable gaps for mounting one or more elastic elements 13 between each pair of consecutive attachment elements 15.

Attachment elements 15, may be configured in a form of a screw that can be threaded into the wall of the heart, or alternatively, these elements may be manufactured in a form of a nail comprising barbs, preferably circumferential barbs along its axis, to allow placement thereof into the heart wall by pushing it into the wall of the heart, such that said barbs prevents its departure therefrom. Additionally, the distal (leading) end portion of the attachment element may be manufactured from a relatively flexible or elastic material, such as, but not limited to, Nitinol, a type of Cobalt alloy, or stainless steel, formed in a helical spring-like shape, such that said distal end portion may be compressed and elongated axially within the heart wall responsive to the systolic and diastolic cycles, respectively.

Advantageously, the flexible/elastic distal (leading) end portion of the attachment element may be manufactured from an absorbable material (e.g., PLLA, PGA, PLA), and/or a suitable polymer, thus providing an attachment element having a stretchable axial length that can be stretched and compressed in response to the diastolic and systolic cycles.

In this way the tangential forces applied by the arms of the elastic elements 13 on the attachment elements 15 expand the heart wall in response to the increased distance effectuated between the attachment elements due to said tangential forces. This arrangement advantageously allows mounting one or more rows of lined elastic elements 13 over the wall of the heart.

In a preferred embodiment of the invention the one or more rows of lined elastic elements 13 are arranged over the left ventricle of the heart in order to improve diastolic function. The one or more rows of lined elastic elements 13 are preferably arranged such that the attachment elements 15s at the extremities of each lined sequence are attached on, or threaded into, the wall of the heart at opposing sides of the septum (S) in order to encircle the LV and in this way attain coverage of the LV wall. In this arrangement, the elastic element advantageously stretches the septum which in turn increases the volume of the LV.

In a typical arrangement each of the rows of lined elastic elements consists of 4 to 7 (depending of the size of the treated heart) elastic elements 13, wherein the force applied by the elastic elements 13s mounted near the septum is generally about, but not limited to, 45±5 grams, and the force applied by the intermediate elastic elements 13 about (but not limited to) 70±10 grams.

Elastic wire or stretchable cord 17 may be mounted over the outer wall of the right ventricle (R) of the heart 10 to further assist heart dilatation during diastol. Elastic wire or stretchable cord 17 may be detachably attached to the attachment elements 15s at the extremities of each lined sequence of elastic elements 13.

If implemented as an elastic wire 17, then the "C" shaped elastic wire 17 is preferably made from a type of elastic biocompatible metal or plastic, such as, but not limited to, stainless steel, Nitinol, suitable alloy or composite compound, preferably from stainless steel, suitable polymer, or an absorbable material (e.g., PLLA, PGA, PLA). Alternatively, the "C" shaped elastic wire 17 may be formed in a shape of a spiral wound metal wire made from one of the aforementioned metals of from a suitable alloy. In this case, elastic wire 17 mainly applies radial forces generally in the range of, but not limited to, 125±75 grams on the attachment elements 15s located at the opposing sides of the septum (S). Elastic wire 17 connected to attachment elements 15s placed at opposing sides of the septum stretches the septum, which surface area is generally about 30% of the surface area of the heart, and thus advantageously increases the volume of the LV. Alternatively, if implemented as a stretchable cord, then stretchable cord 17 is preferably made from a type of biocompatible rubber or elastic plastic material, such as, but not limited to, silicon or rubber, preferably from silicon or rubber. In this case stretchable cord 17 applies pressure over the wall of the heart 10 which advantageously reduces the output of the right ventricle and therefore reduces the risk for pulmonary congestion and edema. More particularly, during the systolic cycle stretchable cord 17 applies pressure on the wall of the right ventricle, and during the diastolic cycle stretchable cord 17 is stretched such that it applies pressure on the wall of the right ventricle and at the same time stretches the septum such that the volume of the LV increases. The force applied by stretchable cord 17 on the wall of the right ventricle reduces the output of the right ventricle and thus reduces the risk of pulmonary edema and the overall blood pressures in the heart.

Figure 2A:
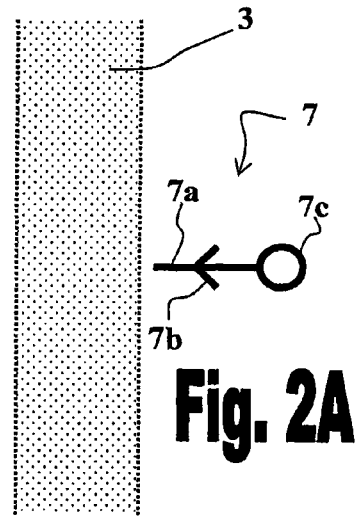
FIGS. 2A to 2D schematically illustrate embodiments of an attachment element comprising two or more barbs.
Figure 2B:
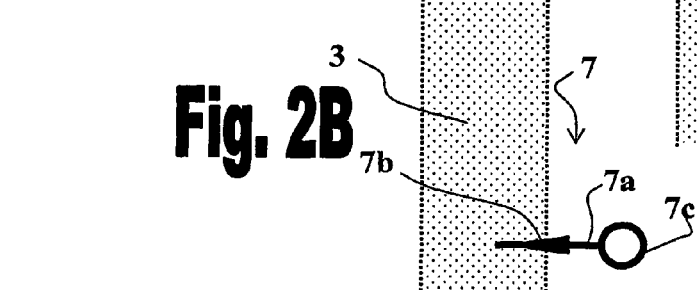
Figure 2C:
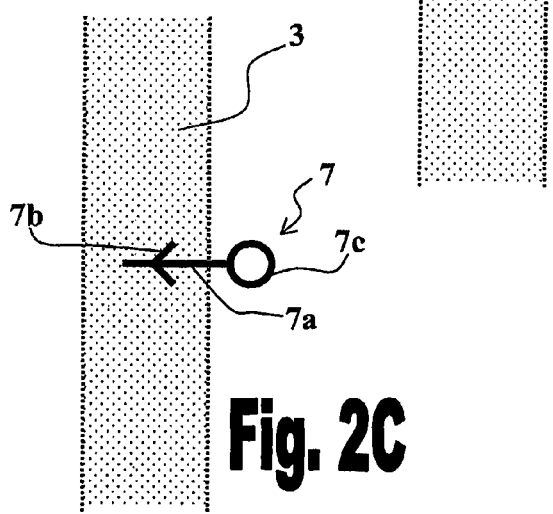

FIGS. 2A to 2C schematically illustrate a preferred embodiment of an attachment element 7 comprising two or more barbs 7b. FIG. 2A illustrates attachment element 7 before attaching it to tissue 3 (e.g., the wall of the heart). Attachment element 7 comprises a nail section 7a having a sharp distal end capable of puncturing and penetrating a tissue, and a head section 7c, attached or formed at the proximal end (relative to the practitioner during attachment thereof) of attachment element 7, said head section is configured to receive and hold detachable means of elastic elements 15.

As exemplified in FIGS. 2A to 2C, barbs 7b are capable of changing their state relative to nail portion 7a of attachment element 7, between an opened state (illustrated in FIGS. 2A and 2C) and a closed state (illustrated in FIG. 2B). FIG. 2B illustrates attachment element 7 during the attachment to tissue 3, during which the sharp distal end of nail section 7a punctures and penetrates into tissue 3, which causes barbs 7b to change into a closed state.

With reference to FIG. 2C, illustrating attachment element after it is attached to tissue 3, after introducing nail section 7a and barbs 7b into tissue 3, barbs 7b change into an open state responsive to slightly pulling attachment element 7 backwardly (proximally). This mechanism anchors attachment element 7 in its attachment location and effectively prevents its departure from tissue 3.

Attachment element may be manufactured by wire pulling or laser cutting from a type of metallic material, such as, but not limited to, stainless steel, cobalt alloy, or nitinol, preferably from nitinol. The length of nail section 7a may generally be in the range of 10 to 30 mm, preferably about 20 mm, and its diameter is preferably in the range of 0.1 to 1.5 mm, Barbs 7b may be implemented by means of a doubled wire configuration attached to nail section 7a, such that one wire of the doubled wire assembly is used for implementing a first barb and the other wire is used for implementing a second barb 7b. The lengths of barbs 7b may generally be in the range of 2 to 20 mm.

Figure 2D:
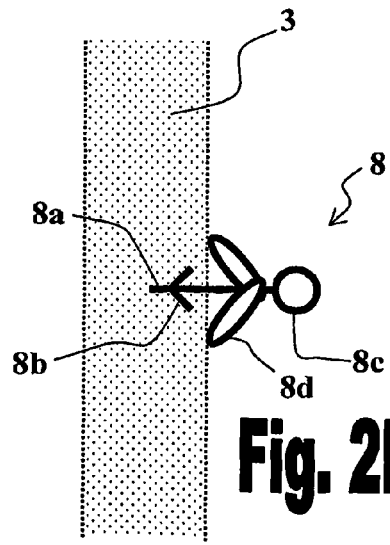

FIG. 2D schematically illustrates another preferred embodiment of an attachment element 8, which further comprises a stopper 8d attached to nail section 8a, near the head section 8c of attachment element 8. Stopper 8d can be implemented by number of (e.g., 2 or 3) slanted arms (or by a conical member) connected to nail section 8a near head section. These slanted arms, or conical member, form a skirt shape in profile which tapers toward its connection point on nail section 8a, for preventing excessive insertion of nail section 8a into tissue 3, thereby preventing changing the state of barbs 8b into a closed state, after attachment to tissue 3. In this way, stoppers 8d secure attachment element 8 in its attachment point, and prevent unintended departure thereof.

Stopper 8d may be manufactured from, for example, stainless steel, cobalt alloy or nitinol, preferably from nitinol. The length and angle relative to nail section 8a, of stopper 8d should be configured to allow penetration of a suitable length (e.g., 1 to 10 mm) of nail section into tissue 3. For example, in one possible embodiment the length of stopper 8d may be about 5 to 30 mm, and its angle about 45° to 135°.

FIGS. 3A to 3D illustrate one preferred embodiment of an elastic element 13a and of attachment elements 15 suitable for mounting the same over the wall of the heart 10. As best seen in FIG. 3A, elastic element 13a is preferably made from an elastic wire formed in a "V"-like shape having spring loop(s) 30 (e.g., torsion spring) at its apex, an anchoring loop 31 at the end of one arm thereof, and a fastening ring 32 at the end of its other arm.

Fastening ring 32 may comprise one or more loops and a widening ring 34 adapted for widening the diameter of the one or more loops of fastening ring 32. Fastening ring 32 may further comprise a saddle 33 formed on the arm section near its loops for assisting in widening said loops by pulling the widening ring 34 towards saddle 33 by means of forceps, pliers, or any other instrument suitable for this purpose.

As best seen in FIG. 3B, attachment element 15 comprises a neck section 15a and an attachment section 15b. Attachment element 15 is preferably made from a curved wire, wherein the attachment section is curved in a shape of a helix (spring) ending in a sharp tip for facilitating puncturing the tissue and threading the attachment section 15b into the wall of the heart. Near the neck section 15a of the attachment element 15 the distances between the helix loops are reduced abruptly to form the neck section 15a wherein the helix loops are tightly arranged in a slightly reduced diameter.

In this way attachment element 15 can be threaded into the wall of the heart by rotating it about its axis and pushing the sharp end of the attachment section 15b against the heart wall, such that it threads into the heart wall as said sharp end penetrates the heart muscle. In this way the portion of the attachment element 15 between the neck 15a and the attachment section 15b acts as a stopper which prevents excess threading thereof.

The diameter of the loops at the end portion of the neck section 15a of the attachment element 15 is preferably slightly enlarged in order to prevent accidental release of the fastening loop therefrom. FIG. 3D illustrates the attachment of elastic elements 13a to attachment elements 15, wherein two elastic elements 13a are mounted by means of attachment elements 15-1, 15-2 and 15-3. In each attachment element (e.g., 15-2) that connects to two adjacent elastic elements 13a, the anchoring loop 31 of one elastic element 13a is placed first over the neck section 15a of the attachment element, and then the fastening ring 32 of the adjacent attachment element is placed thereover by widening its fastening ring 32 and fitting it over said neck section 15a, which blocks disengagement of said anchoring loop 31.

Elastic element 13a may be manufactured by conventional wire (e.g., having circular, elliptic, or rectangular/polygonal cross section) curving techniques, photo chemical etching techniques, laser cutting, or by an erosion process (e.g., using tin films), from a type of elastic metal or plastic, such as, but not limited to, Nitinol, stainless steel, silicon, or a suitable alloy, composite compound, or absorbable material (e.g., PLLA, PGA, PLA), preferably from a Cobalt alloy, having a diameter (thickness) of about 0.45 mm. The length of the arms of elastic element 13a may generally be in the range of 20 to 30 mm, preferably about 23 mm, and the angle α therebetween is about 165±5°. The diameter of spring loop(s) 30 may generally be in the range of 3.5 (for elastic elements mounted at the extremities of the lined sequence) to 5.7 mm, the diameter of fastening ring 32 is preferably about 6±0.5 mm, and the diameter of fastening loop 31 is preferably about 7±1 mm.

Attachment elements 15-1, 15-2, and 15-3, may be manufactured by wire curving processes such as used in conventional spring manufacturing techniques. A suitable thermal treatment may be employed for setting desirable mechanical characteristics and relax curving tensions. Attachment elements 15-1, 15-2, and 15-3, may be manufactured from a type of metal or plastic material, such as, but not limited to, Nitinol, stainless steel, silicon, or a suitable alloy, composite compound, or absorbable material (e.g., PLLA, PGA, PLA), preferably from a Cobalt alloy. Most preferably, attachment elements 15 are made from a curved wire having thickness of about 0.45 mm, and made of a Cobalt alloy.

The total length of attachment element 15 may generally be in the range of 10 to 17 mm, preferably about 15 mm. The diameter of the helix loops in the attachment section 15b may generally be in the range of 3 to 7 mm, preferably about 5 mm, the distance between consecutive loops thereof may generally be in the range of 1 to 3 mm, preferably about 2 mm, and the length of said attachment section may generally be in the range of 6 to 10 mm, preferably about 8 mm. The diameter of the neck section 15a may generally be in the range of 2 to 4 mm, preferably about 3 mm, and its length may generally be in the range of 1 to 3 mm, preferably about 1.5 mm.

Figure 4A:
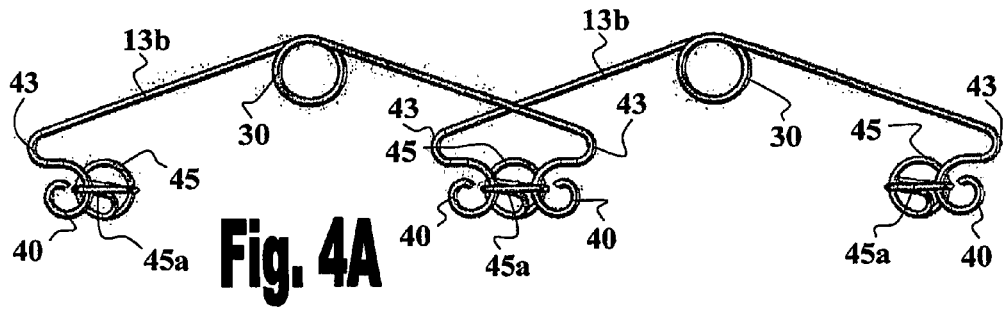
FIGS. 4A and 4B illustrate a preferred embodiment of elastic and attachment elements and their connectivity.
Figure 4B:
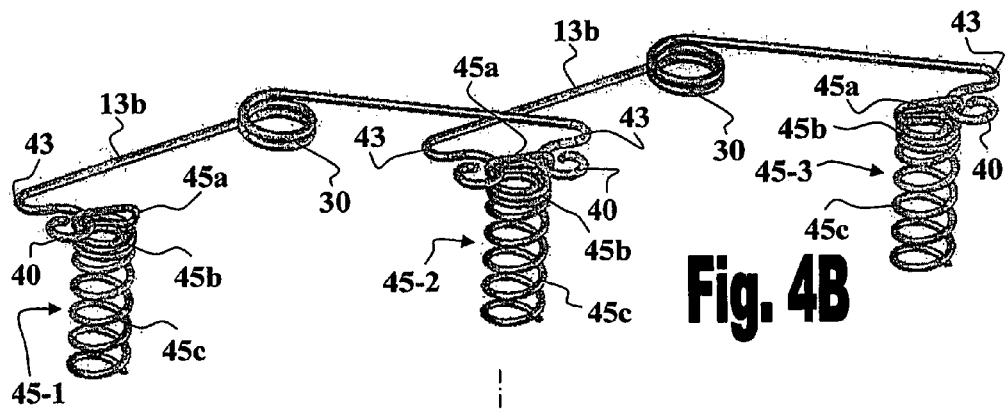

FIGS. 4A and 4B illustrate another preferred embodiment of an elastic element 13b (e.g., torsion spring) and of a suitable attachment element 45 for mounting the same over the wall of the heart 10. Elastic element 13b is preferably made from an elastic wire formed in a "V"-like shape having spring loop(s) 30 at its apex and "G"-shaped curved fasteners 40 at the end of its arms. Curved fasteners 40 may have a spiral shape and they are preferably formed by bending the end sections of the arms towards spring loop(s) 30, thereby forming knees 43, and thereafter bending said end sections away from said spring loop(s) 30 to form a spiral shape therewith. In this way an "S"-like shape (marked by dotted line 4 in FIG. 6B) is formed at the end of each arm, wherein the bottom portion of the "S"-like shape is further curved to form the "G"-shaped curved fasteners 40.

In this preferred embodiment attachment element 45 comprises a head section 45a, a neck section 45b and an attachment section 45c. Attachment element 45 is preferably made from a curved wire, wherein the attachment section 45c is curved in a helix (spring) shape ending in a sharp tip for facilitating puncturing the tissue and threading attachment section 45c into the wall of the heart. Near the neck section

45b of the attachment element 45 the distances between the helix loops are reduced abruptly to form the neck section 45b, which acts as a stopper to prevent excess threading.

The head section 45a is formed in a shape of a loop through which the "G"-shaped ends i.e., curved fasteners 40, of the elastic elements 13b can be passed to engage the same therein. Head section 45a may be formed in any suitable geometrical shape e.g., circular, elliptic, rectangular, however, in this preferred embodiment the head section 45a is formed in a shape of low profile rounded rectangular in order to minimize the mechanical moments exerted thereon by the elastic elements 13b.

Attachment element 45 can be threaded into the wall of the heart by rotation, as was previously described herein above with reference to FIGS. 3A to 3D. FIG. 4B illustrates attachment of elastic elements 13b to attachment elements 45, wherein two elastic elements 13b are mounted by means of attachment elements 45-1, 45-2 and 45-3. The "G"-shaped curved fasteners 40 of each pair of neighboring elastic elements 13b sharing an attachment element (e.g., 45-2) are engaged in the head section 45a of said attachment element such that their arm sections are crossed near knees 43 and their "G"-shaped loops are pressed against the opposing sides of said head section. This configuration substantially enhances the stability of the elastic and attachment elements arrangement due to the opposing pulling forces exerted on the attachment elements 45 by the pairs of neighboring elastic elements 13b.

Elastic element 13b may be manufactured using conventional wire (e.g., having circular, elliptic, or rectangular/polygonal cross section) curving techniques, photo chemical etching techniques, laser cutting, or by an erosion process (e.g., using tin films) from a type of elastic metal or plastic, such as, but not limited to, Nitinol, stainless steel, silicon, or a suitable alloy, composite compound, or absorvable material (e.g., PLLA, PGA, or PLA), preferably from a Cobalt alloy, having a diameter (thickness) of about 0.45 mm. The length of the arms of elastic element 13a may generally be in the range of 20 to 30 mm, preferably about 23 mm, and the angle $\alpha$ therebetween is about 165±5°. The diameter of spring loop(s) 30 may generally be in the range of 3.5 mm (for elastic elements mounted at the extremities of the lined sequence) to 5.7 mm, and the diameter of the "G"-shaped curved fasteners 40 is preferably about 2±1 mm.

Attachment element 45 may be manufactured by a wire curving processes, such as used in conventional spring manufacturing techniques, which may be followed by a suitable thermal treatment to set mechanical characteristics and relax curving tensions. Attachment element 45 may be manufactured from a type of metal or plastic material, such as, but not limited to, Nitinol, stainless steel, silicon, or a suitable alloy, composite compound, or absorvable material (e.g., PLLA, PGA, or PLA), preferably from, a Cobalt alloy. Most preferably, attachment elements 45 are made from a curved wire having thickness of about 0.45 mm and made of a Cobalt alloy. The total length of attachment element 45 may generally be in the range of 8 to 18 mm, preferably about 15 mm. The diameter of the helix loops in the attachment section 45c may generally be in the range of 3 to 6 mm, preferably about 5 mm, the distance between consecutive loops thereof may generally be in the range of 1 to 3 mm, preferably about 2 mm, and the length of said attachment section may generally be in the range of 6 to 12 mm, preferably about 8 mm. The diameter of the neck section 45b may generally be in the range of 2 to 6 mm, preferably about 5 mm, and its length may generally be in the range of 0.5 to 2 mm, preferably about 1.5 mm.

Figure 5A:
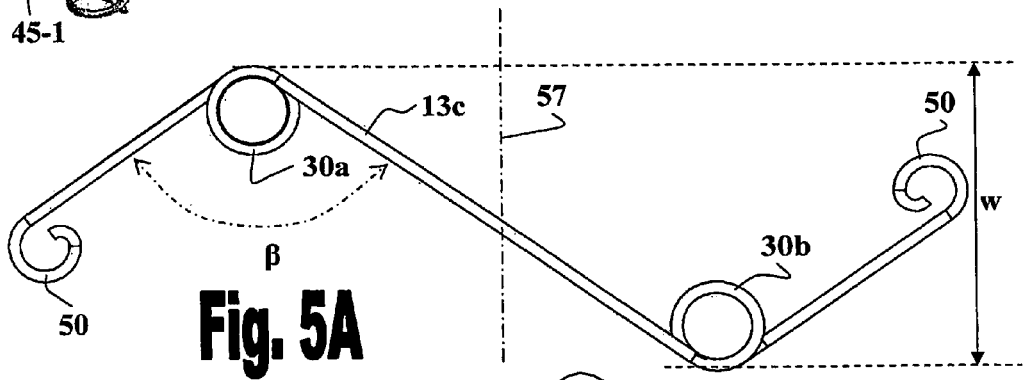
FIGS. 5A and 5B respectively illustrate upper and perspective views of another preferred embodiment of the elastic element and of a respective attachment element.
Figure 5B:
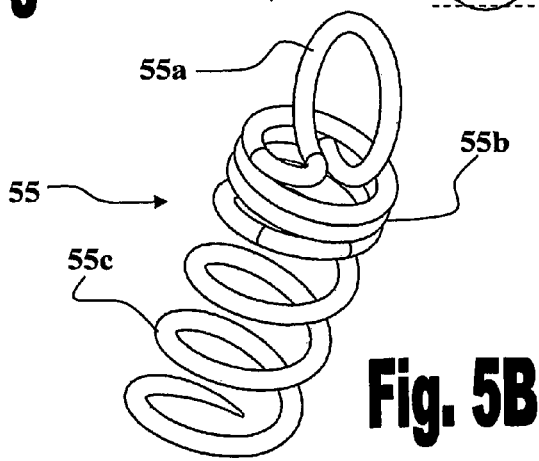
Figure 5C:
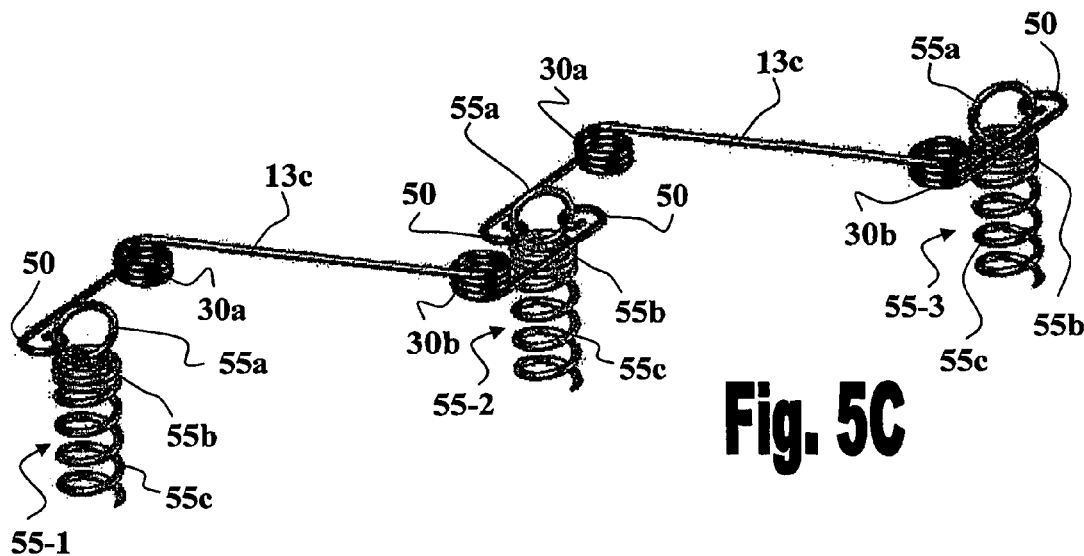
FIG. 5C shows a perspective view of the connectivity of elastic and attachment elements shown in FIGS. 5A and 5B.

FIGS. 5A to 5C illustrate yet another preferred embodiment of an elastic element 13c and respective attachment element 55 used for mounting it on the wall of the heart (not shown). Elastic element 13c is formed in a shape of a wire spring comprising two or more angled portions along its length having a spring loop 30 at each apex, for example, spring loops 30a and 30b (e.g., torsion springs) as shown in FIGS. 5A and 5C. The spatial width (w) of the elastic elements 13c in this preferred embodiment may be advantageously reduced since greater forces may be applied this way with shorter wire arms. Curved fasteners 50 are formed at the extremities of elastic element 13c by curving a spiral-like loop shape at the end portions at said extremities, where said spiral-like loops are formed in opposite directions relative to a symmetry axis 57.

As shown in FIG. 5C the spiral shaped curved fasteners 50 of each pair of neighboring elastic elements 13c sharing an attachment element (e.g., 55-2) are engaged in the head section 55a of said attachment element such that said spiral-shaped loops are pressed against the opposing sides of the head section 55a of said attachment element. This arrangement substantially reduces the spatial width of the device to about 2 w while also improving its stability due to the opposite pulling forces exerted by the neighboring elastic elements on the attachment elements.

As best seen in FIG. 5B, attachment elements 55 comprises an attachment section 55c, a neck section 55b, and a head section 55a, having substantially similar shape and dimensions to those sections in attachment element 45 described herein above with reference to FIG. 4B. While the head section 55a of attachment element 55 in FIG. 5B has a circular shape, it may be configured differently according to the implementation requirements, for example, it may be formed in an elliptic, rectangular, polygonal, or any other suitable geometrical shape.

Elastic elements 13c and attachment elements 55 may be manufactured by using the same manufacturing techniques and from the same materials as elastic elements 13b and attachment elements 45 described hereinabove. The length between an anchoring loop 50 and the neighboring spring loop 30 is generally in the range of 10 to 15 mm, preferably about 12.5 mm, the length between the spring loops (e.g., 30a and 30b) is generally in the range of 20 to 30 mm, preferably about 23 mm, and the angle $\beta$ between the arms of elastic element 13c is preferably in the range of 90±15°.

The arrangement of elastic elements 13c and attachment elements 55, as shown in FIG. 5C, advantageously provides the same functionality as in the previously described embodiments of the invention while preventing friction between neighboring elastic elements as may evolve in the arrangement of elastic elements 13b and attachment elements 45 described with reference to FIGS. 4A and 4B.

Figure 6A:
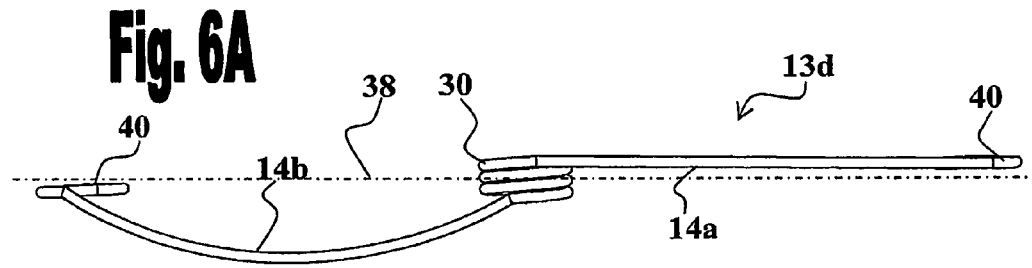
Figure 6B:
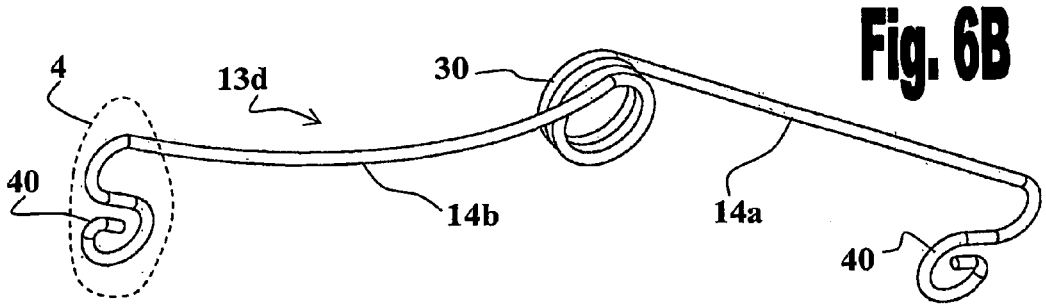
Figure 6C:
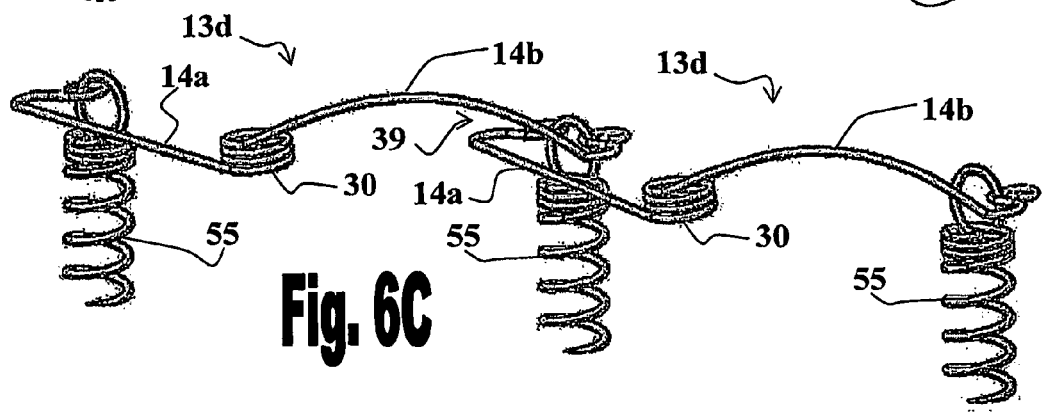

FIGS. 6A to 6C illustrate a preferred embodiment of the elastic element, designated by reference numeral 13d, having an arm which at least a portion of its length is curved.

Elastic element 13d is substantially similar to elastic element 13b described hereinabove with reference to FIGS. 4A and 4B. As best seen in the upper view shown in FIG. 6A, elastic element 13d comprises a first arm 14a which is relatively straight, and a second arm 14b which is curved relative to longitudinal axis 38 of attachment element 15d.

As illustrated in FIG. 6C, wherein the attachment of elastic elements 13d to attachment elements 55 is exemplified, second arms 14b of elastic elements 13d are curved such that the straight arm 14a of the adjacent elastic element may be passed beneath second arm to engage the head section of the attachment element 55 while maintaining a gap 39 therebetween.

The attachment elements (e.g., 7, 15, 45 or 55) may be further used for drug delivery by coating them with one or more layers of drug-containing coats (not illustrated). FIG. 7 schematically illustrates such drug release (designated by arrows 56) of attachment element 55 into tissue 3. The one or more drug-containing coats are preferably adapted to provide a gradual delayed release (e.g., about 1 to 12 months) of medicaments (e.g., Sirolimus, Taxol, Batimistat, BCP671) into the tissue to which they are attached. The medicaments may be used for promoting cell growth and thereby prevent rejection of the device by the body. Alternatively, the one or more drug-containing coats may be adapted to gradually release portions of the medicaments within predetermined time periods, the duration of which may be controllably set by the practitioner e.g. by the choice of coating material, coating density, coating method etc.

Alternatively or additionally, the attachment elements may be manufactured from a hollow conduit (not shown) containing the medicaments thereinside, and having small drug release apertures (e.g., about 0.001 to 0.15 mm) capable of providing the gradual drug release needed.

FIGS. 8A and 8B illustrate one preferred embodiment of a gripping tool 60 designed to assist in threading attachment elements (e.g., 55 shown in FIG. 5B) in a tissue (not shown). Gripping tool 60 comprises a hollow handle 61 which interior may be accessed via a front opening 61o, and a gripping element 62 capable of gripping the head section 55a of attachment element 55. Handle 61 is configured to receive gripping element 62 into its interior via opening 61o. Handle 61 may further comprise a flange 61a used for buffering between handle 61 and an attachment element 55, and for assisting in releasing the attachment element 55 held by the gripping element 62.

As seen in the exploded view of gripping tool 60 shown in FIG. 8B, gripping element 62 comprises a slit 62a capable of receiving and gripping head section 55a of attachment element 55. Gripping element 62 is inserted into handle 61 such that slit 62a may be accessed via opening 61o to allow introducing head section 55a of attachment element 55 thereinto. After introducing; head section 55a of attachment element 55 into slit 62a and establishing a firm grip thereover, the practitioner may thread attachment element 55 into a tissue by holding handle 61 of gripping tool 60 and pressing and rotating attachment element 55 against the tissue. In this way the sharp end of attachment section 55c penetrates into the tissue and attachment section 55c is threaded thereinto until flanged section 61a of handle 61 is pressed against the tissue and the grip of gripping tool 60 over head section of attachment element 55 is released.

Handle 61 may be manufactured by extrusion, for example, from a type of nylon or polyurethane, preferably from nylon 12. The length of handle 61 may generally be in the range of 15 to 50 mm, preferably about 25 mm, and its diameter may be in the range of may generally be in the range of 5 to 8 mm. Gripping element 62 may be manufactured by extrusion from, for example, a type of silicon, Teflon, or polyurethane, preferably from silicon. The length of gripping element 62 may generally be in the range of 15 to 50 mm, preferably about 20 mm, and its diameter may be in the range of may generally be in the range of 3 to 7 mm.

FIGS. 9A to 9D schematically illustrate another preferred embodiment of a gripping tool designated by reference numeral 70. In this preferred embodiment the gripping and the release of said gripping over the head section of the attachment element is carried out by means of a depressible actuator 72 laterally protruding from gripping tool 70. With reference to the longitudinal section view shown in FIG. 9D, gripping tool 70 comprises a hollow housing 71, a gripping element 73, a hollow shaft 76 capable of receiving a proximal section of said gripping element 73, a spring 75 disposed in the interior of housing 71, and a depressible actuator 72.

Figure 9A:
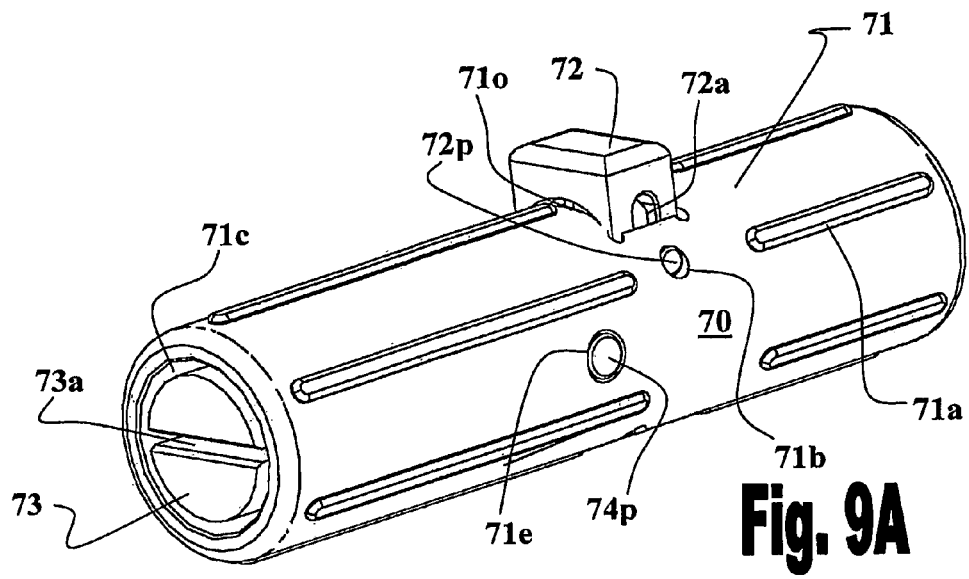
Figure 9B:
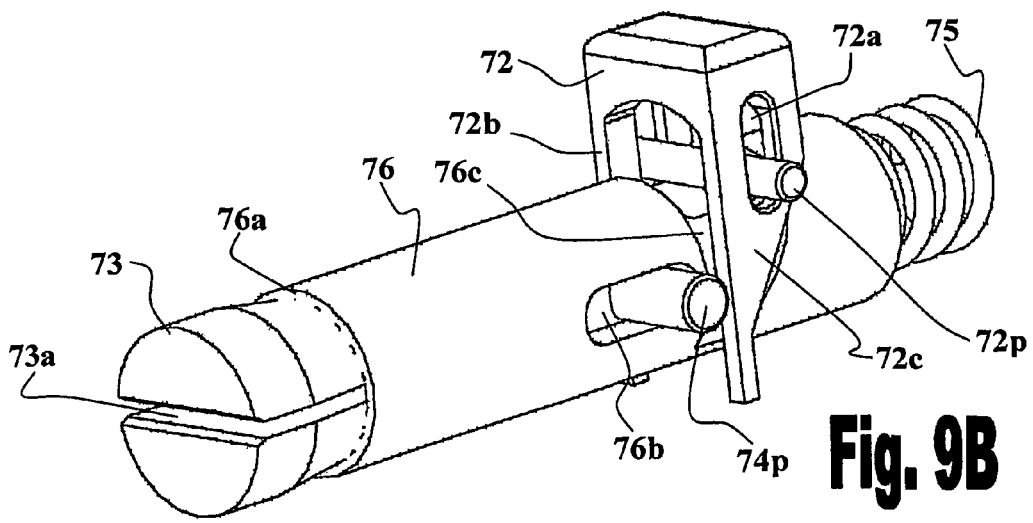
Figure 9C:
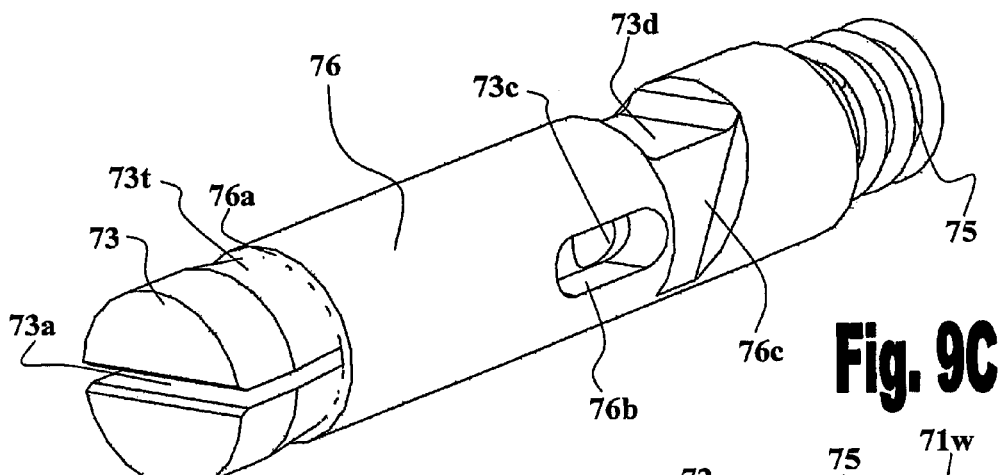
Figure 9D:
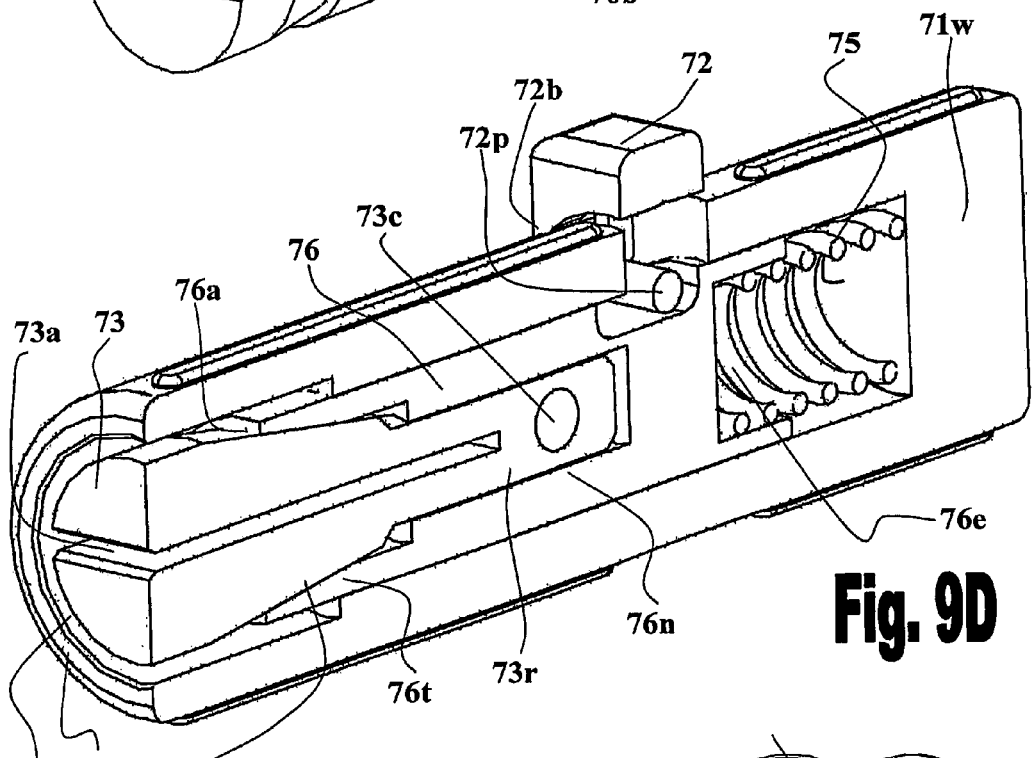

Gripping element 73 comprises a tapering section 73t which tapers proximally towards a proximal slender section 73r thereof, and a slit 73a passing along tapering section 73t and along a portion of slender section 73r, wherein slit 73a is capable of receiving the head section (e.g., 55a) of an attachment element. As can be seen in FIGS. 9A and 9B, gripping element 73 is affixed inside housing 71 by means of a pin 74p configured to be received in two opposing holes 71e provided in the wall of housing 71 and to pass in a bore 73c (shown in FIG. 9D) provided in slender section 73r.

Hollow shaft 76 comprises a distal opening 76a (shown in FIGS. 9B and 9D) through which slender section 73r and tapering section 73t of gripping element 73 are introduced thereinto. The interior of hollow shaft 76 comprises a tapering section 76t which tapers proximally towards a narrow passage 76n. Tapering section 76t and narrow passage 76n of hollow shaft 76 are configured to receive slender section 73r and tapering section 73t, respectively, of gripping element 73, and allow hollow shaft to slide thereover. Hollow shaft 76 comprises two lateral grooves 76b (shown in FIG. 9C) passing along longitudinal portions in opposing sides thereof and adapted to allow passage of pin 74p therethrough, such that hollow shaft can be moved distally or proximally thereover.

In this way hollow shaft 76 is movably disposed inside housing 71 wherein spring 75 pressed against its proximal end and received in a proximal socket 76e thereof is utilized for restoring its initial state. The proximal movements of hollow shaft 76 are limited by tapering section 73t of hollow shaft 76, and its proximal movements are performed against the forces applied by spring 75.

As shown in FIG. 9B, hollow shaft 76 comprises two lateral grooves 76c provided at opposing sides thereof, said lateral grooves 76c are adapted to receive lateral arms 72c of depressible actuator 72, said lateral arms 72c are adapted to move up or down in grooves 76c. Depressible actuator 72 is movably attached to hollow housing 71 by means of pin 72p, passing through vertical grooves 72a provided in the upper portions of arms 72c of depressible actuator 72, and attached in two corresponding bores 71b provided in the wall of hollow housing 71. In this way, depressible actuator 72 can be moved up or down through opening 71o provided in hollow housing 71.

The proximal sides of lateral arms 72c of depressible actuator 72, and the proximal sides of lateral grooves 76c, are configured with a corresponding slanted sections, such that whenever depressible actuator 72 is pressed downwardly the slanted sections of lateral arms 72c slide along the corresponding slanted sections of lateral grooves 76c of hollow shaft and force it to move proximally against the force applied by spring 75. During these proximal movements of hollow shaft 76 a portion of tapering section 73t of gripping element 73 is moved out of hollow shaft 76 via its distal opening 76a, thereby releasing the pressure applied thereover by tapering section 76t of hollow shaft 76 and allowing slit 73a to expand.

When the practitioner releases depressible actuator 72 hollow shaft 76 is moved distally due to the force applied by spring 75, which in turn forces depressible actuator to move upwardly, and a portion of tapering section 73t of gripping element 73 is moved back into hollow shaft 76 via distal opening 76a. Whenever said portion of tapering section 73t of gripping element 73 is moved into hollow shaft 76, tapering section 73t is pressed against tapering section 76t of hollow shaft 76 which forces slit 73a to contract.

In this way gripping tool 70 may be used for gripping an attachment element by pressing down depressible actuator 72 for advancing gripping element 73 distally to have slit 73*a* in an expanded state and allow the practitioner to introduce the head section of the attachment element thereinto. Thereafter, the practitioner releases depressible actuator which in turn retracts gripping element 73 proximally and tightens the grip over the head section. The practitioner can then thread the attachment element into the tissue by means of the gripping tool 70, and thereafter release the grip over the head section of the anchoring element by pressing down depressible actuator 72.

Figure 10A:
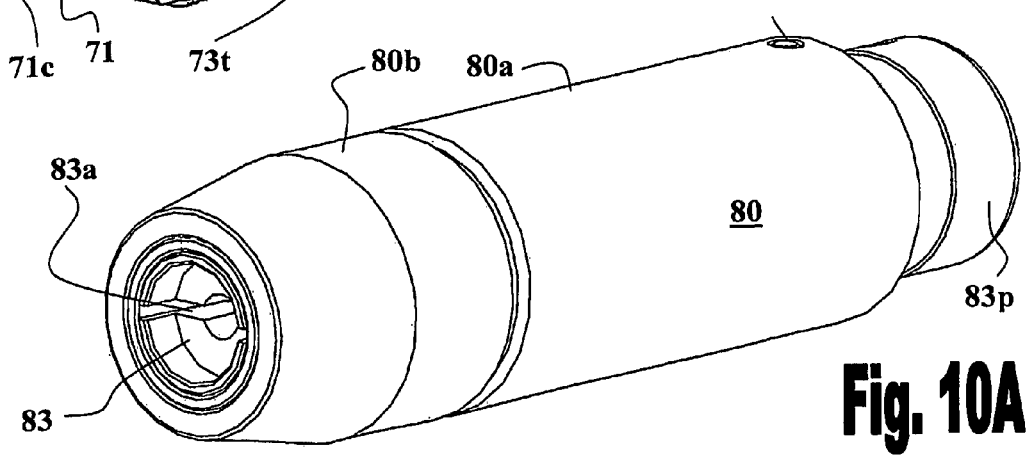
Figure 10B:
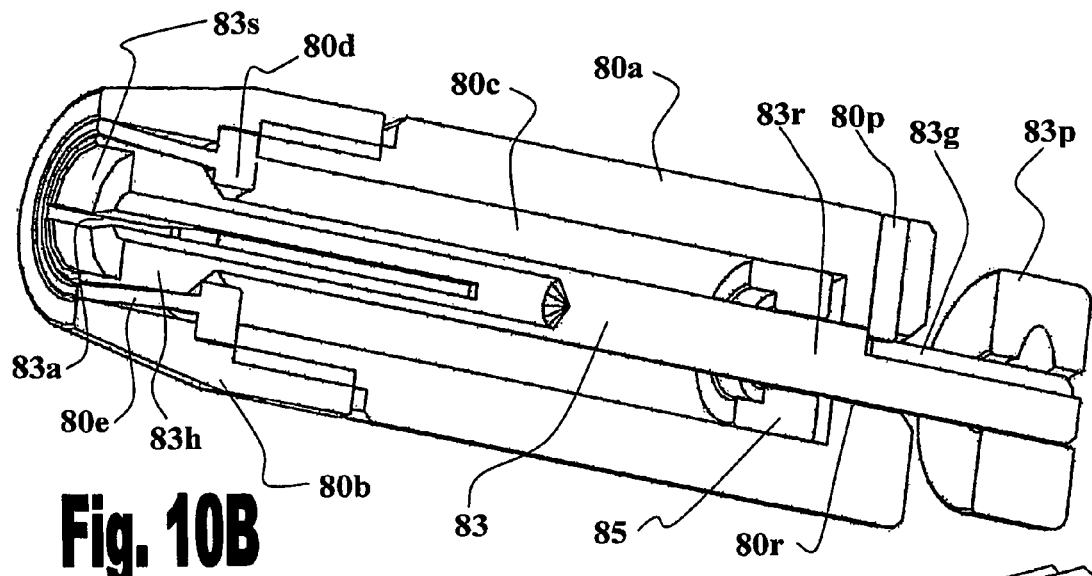
Figure 10C:
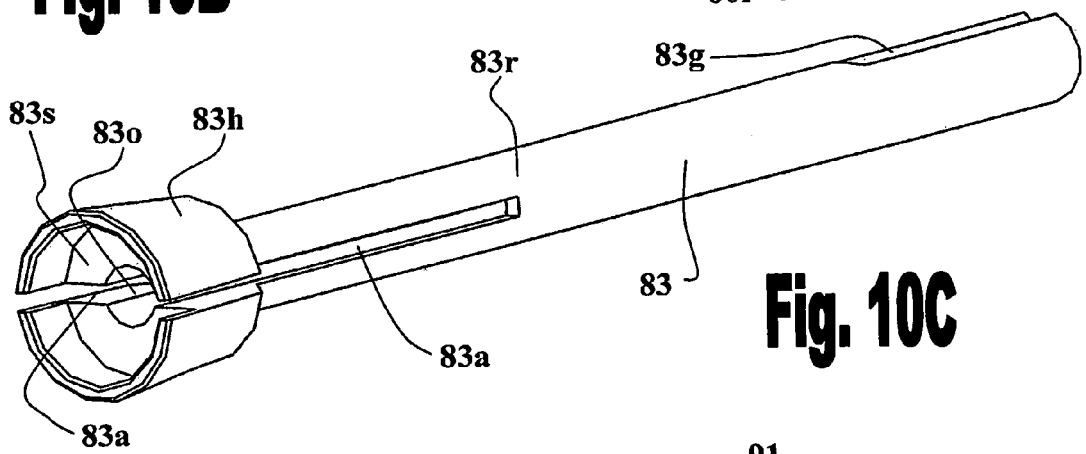

FIGS. 10A to 10C illustrate another implementation of a gripping element 80 of the invention having a proximal actuation. FIG. 10A shows a perspective view of gripping element 80 comprising a hollow body 80*a* having a distal cover 80*b* fitted over a distal end section thereof, and a gripping tool 83. With reference to the longitudinal section view shown in FIG. 10B, hollow body 80*a* comprises a proximal bore 80*r*, an inner lumen 80*c* ending in shoulders 80*d* formed at a distal portion thereof which further comprises a proximally tapering section 80*e*. Gripping element 83 is made from a shaft 83*r* comprising a gripping head 83*h* having a distal socket 83*s*. As can be seen in FIG. 10C, showing a perspective view of gripping element 83, a distal section of gripping element 83 comprises a longitudinal slit 83*a* which may comprise an inner bore 83*o* passing therealong for ensuring easy opening of the gripping head 83*h*, said longitudinal slit 83*a* splits gripping head 83*h* and a distal portion of shaft 83*r* into an upper and lower portions.

As seen in FIG. 10B, gripping element 83 is movably disposed inside the assembly formed by hollow body 80*a* and distal cover 80*b* such that a proximal section of shaft 83*r* is passed through bore 80*r* of hollow body 80*a*, and a distal section of shaft 83*r* is passed through the opening formed by shoulders 80*d*. Gripping head 83*h* of gripping tool 83 tapers proximally to allow snugly introducing it into proximally tapering section 80*e* of hollow body 80*a*. The proximal end section of shaft 83*r* comprises a groove 83*g* configured to receive the end of pin 80*p* attached in a bore formed in the wall of hollow body 80*a*. Groove 83*g* and pin 80*p* prevents rotations of gripping element 83 about its longitudinal axis.

Gripping tool 70 preferably has a cylindrical shape, and it may be manufactured, for example, from a type of stainless steel, plastic, or polyurethane, preferably from plastic, by means of injection. The length of gripping tool 70 may generally be in the range of 20 to 70 mm, preferably about 40 mm, and its diameter may generally be in the range of 5 to 10 mm, preferably about 7 mm. The length of hollow shaft may generally be in the range of 20 to 70 mm, preferably about 30 mm, and its diameter may generally be in the range of 3 to 10 mm, preferably about 6 mm. The length of tapering section 73*t* of gripping tool 73 may generally be in the range of 3 to 13 mm, preferably about 6 mm, and the diameter of its distal end may generally be about 3 to 10 mm. The length of proximal slender section 73*r* of gripping tool 73 may generally be in the range of 2 to 10 mm, preferably about 3 mm, and its diameter may generally be in the range of 3 to 10 mm, preferably about 5 mm. The length of slit 73*a* is preferably about 3 to 10 mm.

In FIGS. 10A and 10B gripping head 83*h* is shown in a first state of gripping tool 80, wherein gripping head 83*h* is placed inside proximally tapering section 80*e*. In this state the upper and lower portions of gripping head are pressed one towards the other by proximally tapering section 80*e*, which tightens slit 83*a*. By pressing on pressing disk 83*p* attached to the proximal end of gripping element 83 the practitioner may change gripping tool into its second state (not shown), wherein shaft 83*r* is moved distally inside hollow body 80*a* such that gripping head 83*h* leaves proximally tapering section 80*e* of hollow body 80*a*. In this state the practitioner may introduce the head section of an attachment element into slit 83*a* which is typically slightly expanded in said second state.

After introducing the head section of an attachment element into slit 83*a*, the practitioner releases the pressure over the pressing disk 83*p* which causes gripping element to retract proximally such that gripping head 83*h* is mostly returned into proximally tapering section 80*e* of hollow body 80*a* and slit 83*a* tightens about the head section of the attachment element to provide a firm grip thereover. The practitioner may then thread the attachment element into a tissue by means of gripping element and thereafter release the gripping over head section of the attachment element by pressing on pressing disk 83*p* and retracting gripping tool 80 proximally to release the attachment element.

Gripping tool 80 preferably has a cylindrical shape, and it may be manufactured, for example, from a type of stainless steel, plastic, or polyurethane, preferably from plastic, by means of injection. The length of gripping tool 80 may generally be in the range of 20 to 50 mm, preferably about 35 mm, and its diameter may generally be in the range of 3 to 8 mm, preferably about 6 mm. The length of hollow body 80*a* may generally be in the range of 10 to 30 mm, preferably about 15 mm, its outer diameter may generally be in the range of 5 to 10 mm, preferably about 7 mm, and its inner diameter may generally be in the range of 5 to 8 mm, preferably about 7 mm.

The length of gripping element 83 may generally be in the range of 30 to 70 mm, preferably about 50 mm, and the diameter of its shaft 83*r* may generally be about 2 to 5 mm. The length of gripping head 83*h* may generally be in the range of 3 to 6 mm, preferably about 4 mm, and the diameter of its distal end may generally be about 3 to 8 mm. The length of slit 83*a* is preferably about 3 to 8 mm.

Figure 11A:
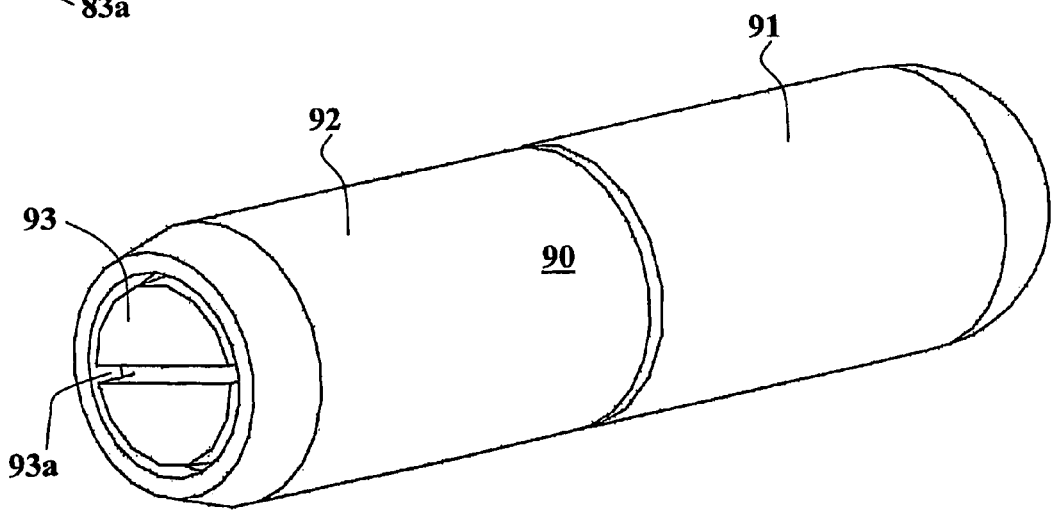
Figure 11B:
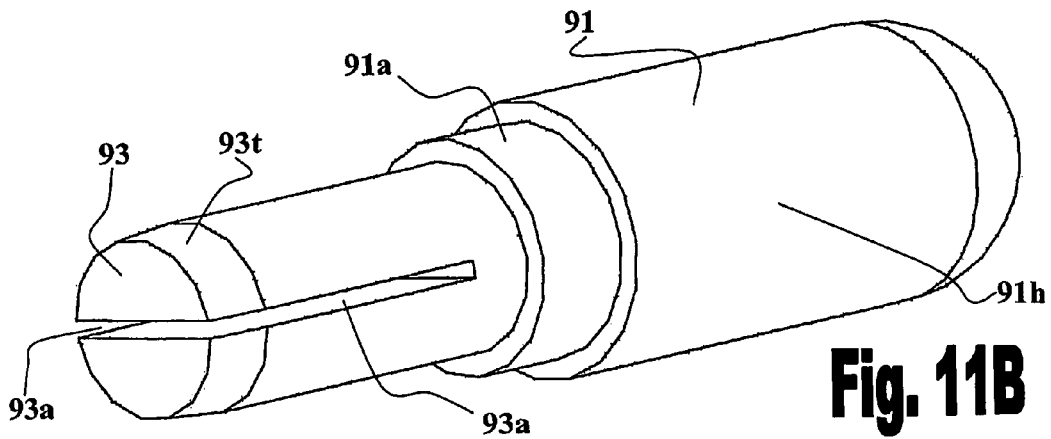
Figure 11C:
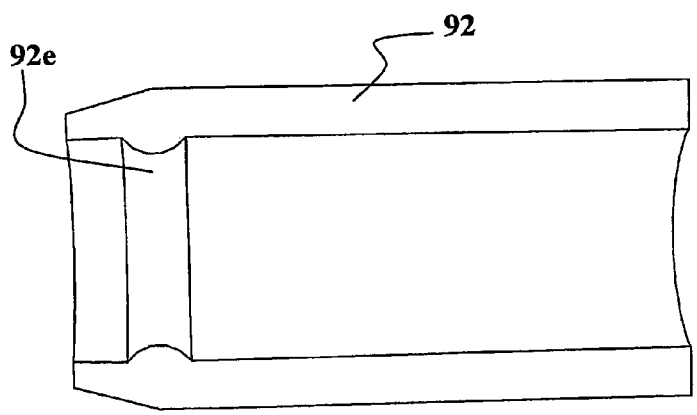

FIGS. 11A to 11C illustrate yet another gripping tool implementation 90 of the invention having a rotary gripping mechanism. As shown in the perspective view shown in FIG. 11A, gripping tool 90 comprises a main body 91 having a slidable and rotatable sleeve 92 mounted over a distal section thereof. FIG. 11B shows a perspective view of main body 91 which comprises a handle portion 91*h*, threaded section 91*a*, and a gripping distal portion 93 comprising a longitudinal slit 93*a*. As can be seen in the longitudinal-section view of slidable and rotatable sleeve 92 shown in FIG. 11*c*, an annular protrusion 92*e* is formed on the inner wall of slidable and rotatable sleeve 92, said annular protrusion 92*e* is configured to apply pressure on a distally tapering end section 93*t* of gripping distal portion 93 of main body 91. Slidable and rotatable sleeve 93 may further comprise threading formed in a proximal end section of its inner wall.

This configuration permits slidable and rotatable sleeve 92 to be advanced and retracted relative to main body 91 by rotating the same thereover. Such advancing and retracting alter the stated of gripping distal portion 93 between two states. In the first state slidable and rotatable sleeve 92 is advanced distally and the pressure applied by annular protrusion 92*e* over distally tapering end section 93*t* of gripping distal portion 93 is released, and in turn, longitudinal slit 93*a* is slightly expanded. In this state the practitioner may introduce the head section of an attachment element into longitudinal slit 93*a*. When slidable and rotatable sleeve 92 is retracted proximally such that the pressure applied by annular protrusion 92*e* over distally tapering end section 93*t* of gripping distal portion 93 is restored, longitudinal slit 93*a* is tightened and a firm grip over head section of attachment element is obtained. The practitioner may thread the attachment element into the tissue by means of gripping tool 90, and release the grip over attachment element by advancing slidable and rotatable sleeve 92 distally.

Gripping tool 90 preferably has a cylindrical shape, and it may be manufactured, for example, from a type of stainless steel, plastic, or polyurethane, preferably from plastic, by means of injection. The length of gripping tool 90 may generally be in the range of 20 to 60 mm, preferably about 35 mm, and its diameter may generally be in the range of 3 to 10 mm, preferably about 6 mm. The length of slidable and rotatable sleeve 92 may generally be in the range of 15 to 35 mm, preferably about 20 mm, and its inner diameter may generally be in the range of 3 to 10 mm, preferably about 5 mm. The length of gripping distal portion 93 may generally be in the range of 15 to 65 mm, preferably about 40 mm, and its diameter may generally be about 3 to 8 mm. The length of slit 93a is preferably about 10 to 30 mm.

FIGS. 12A to 12F show perspective views of instruments designed for guiding the practitioner in determining suitable distances between adjacent attachment elements, and between rows of such elements on the wall of the heart, by means of distance indicating arms. The instrument 100 shown in FIG. 12A may be used for designating two different distances by means of two distance indicating arms, 100h and 100g, attached, or formed, vertical to shaft 100r of instrument 100. distance indicating arms, 100h and 100g, are configured to give the practitioner means for determining a suitable distances between adjacent attachment elements and for determining a suitable distance between adjacent rows of attachment elements, respectively. This is carried out by placing one end of a distance indicating arm at the location of a previously mounted attachment element, or row of such elements, and using the other end of said distance indicating arm to determine the distance to a location wherein another such attachment element, or row of such elements, is to be mounted.

Figure 12A:
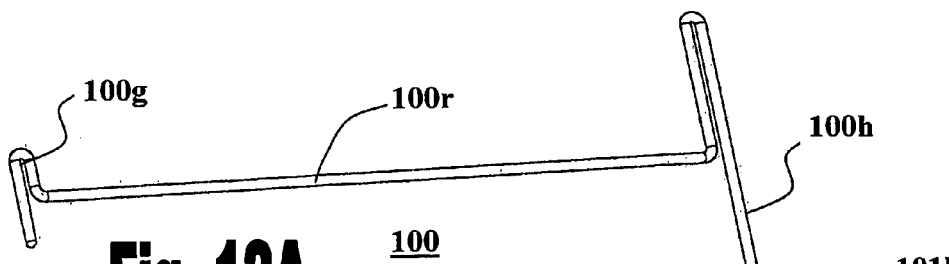

As shown in FIG. 12A, instrument 100 may be manufactured from a wire, strip or rod, shaped into the illustrated form. More particularly, the extremities of shaft portion 100r of instrument 100 may be bent in a 90° angle relative to said shaft 100r and then bent again in a 270° relative to said 100r to form distance indicating arms 100h and 100g, which forms "T"-shaped structures.

Figure 12B:
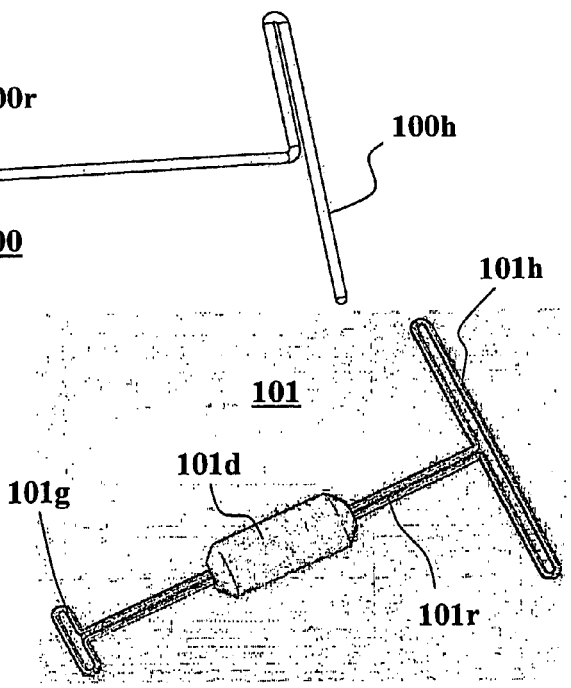

FIG. 12B illustrates a similar instrument in principle, having two distance indicating arms, 101g and 101h, attached, or formed, vertical to shaft 101r, which forms "T"-shaped structures, said shaft 101r optionally comprises handle 101d, said optional handle is preferably placed more or less at the center of shaft 101r. Instrument 101 may be also manufactured from a single piece of wire, strip or rod, such that each part of instrument 101 is comprised of two sections of the wire, strip or rod.

Figure 12C:
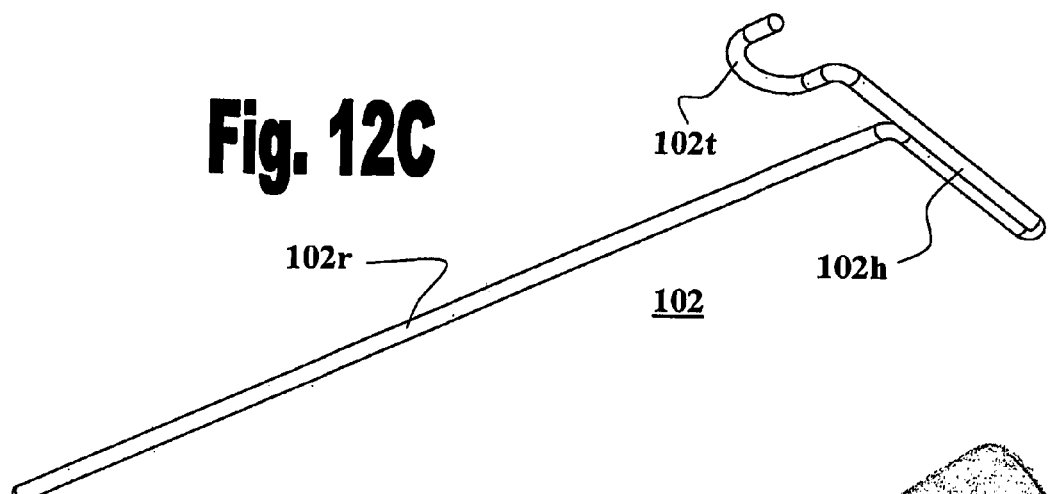

The instrument 102 illustrated in FIG. 12C is designed for designating a distance for mounting an adjacent attachment element by means of a distance indicating arm 102h, attached or formed vertical to shaft 102r, and an acceptable tolerable deviation within which the attachment element may be mounted by means of a "U"-shaped portion 102t provided at one end of distance indicating arm 102h.

Figure 12D:
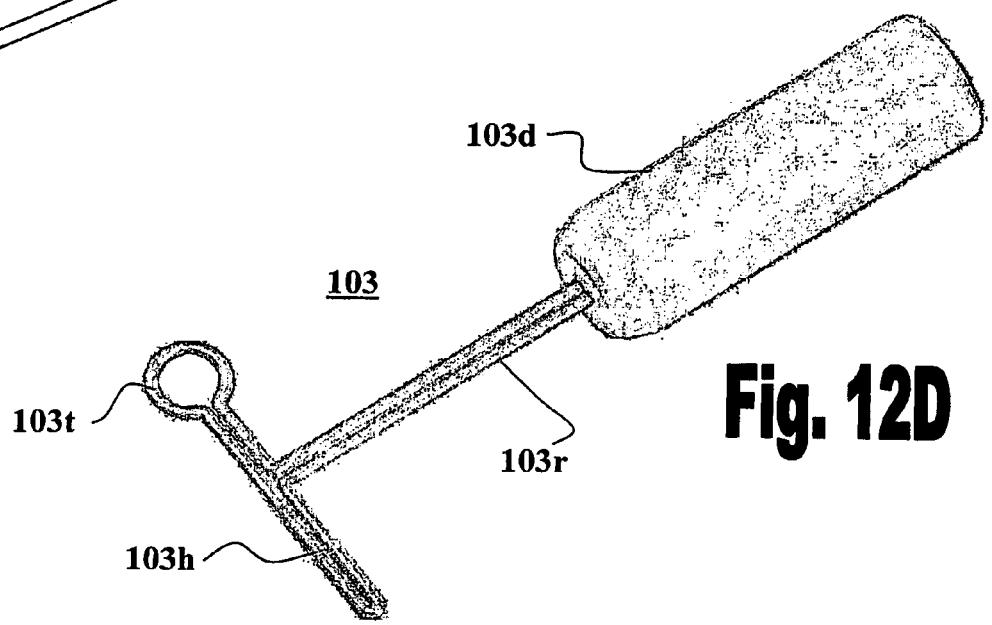

Instrument 103 shown in FIG. 12D is similar in principle, i.e., the distance for mounting an adjacent attachment element is determined by means of a distance indicating arm 103h, attached or formed vertical to shaft 103r, and the acceptable tolerable deviation within which the attachment element may be mounted is determined by means of a ring 103t provided at one end of distance indicating arm 103h. Handle 103d is optionally placed at the proximal end of shaft 103r.

Figure 12E:
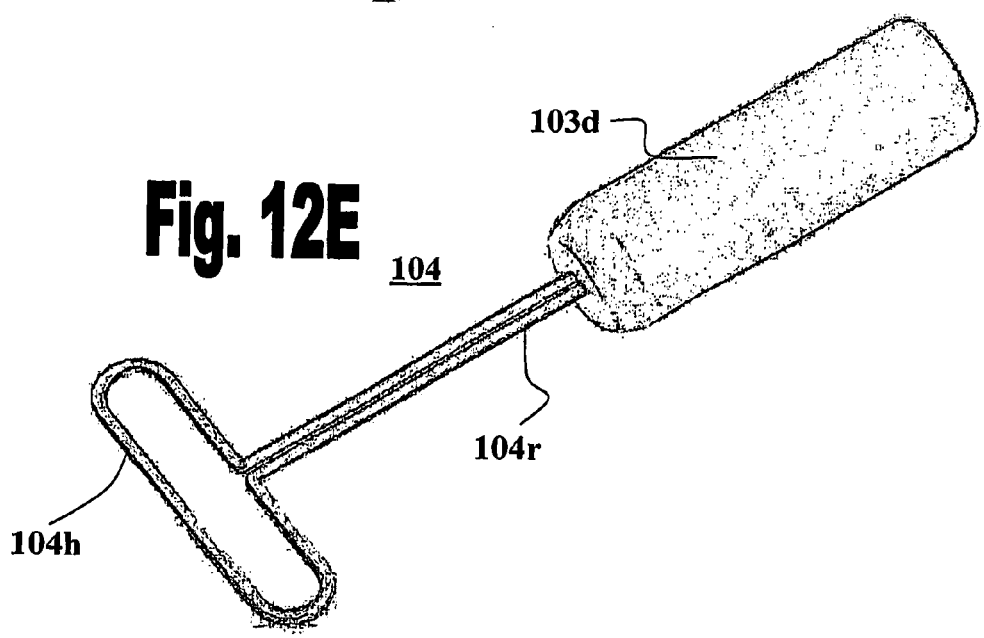

FIG. 12E illustrates an instrument 104 wherein the distance indicating arm 104h attached, or formed, vertical to shaft 104r, forms an elongated loop, such that the adjacent attachment element placed therewith may be attached to the wall of the heart through said elongated loop of distance indicating arm 104h. This embodiment permits the practitioner to determine the distance of the adjacent attachment element by placing the previously installed attachment within the elongated loop of distance indicating arm 104h near one end thereof, aligning distance indicating arm 104h such that the other end of the elongated loop is placed at the location wherein the adjacent attachment element is to be installed, and then installing said adjacent attachment element through said elongated loop near said other end of the elongated loop.

Figure 12F:
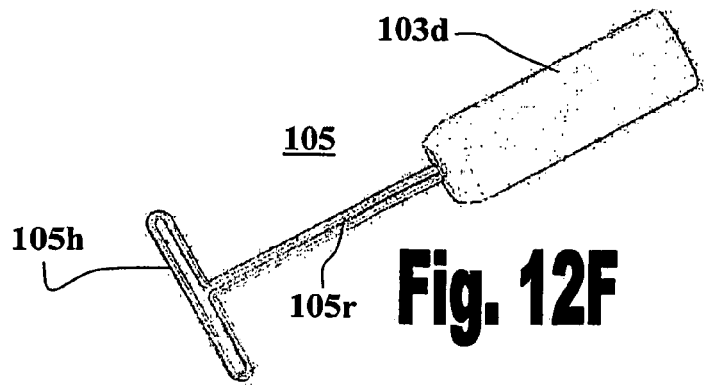

FIG. 12F illustrates an instrument 105 having a distance indicating arm 105h attached, or formed, vertical to shaft 105r, which permits the practitioner to determine the distance to a location wherein the adjacent attachment element is to be mounted by placing the distance indicating arm 105h between the attachment elements.

Figure 13:
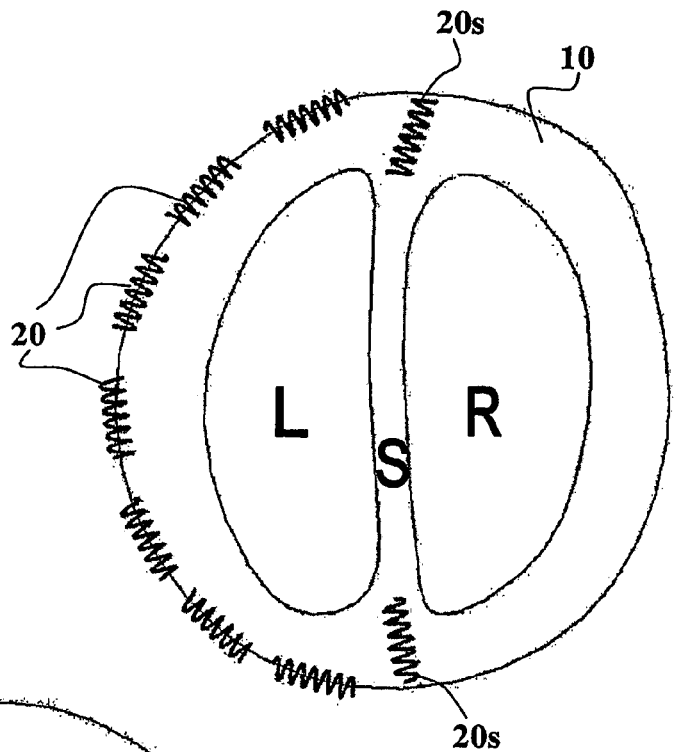
FIG. 13 illustrates a preferred embodiment for treating ventricular dysfunctions which employs compressible elements that are threaded into the wall of the heart.

FIG. 13 illustrates another preferred embodiment of the invention for assisting ventricular heart function wherein one or more compressible elements 20 are threaded into the wall of the heart 10. Compressible elements 20 may be threaded into the wall of the ventricle when heart 10 is fully dilated, or alternatively when heart 10 fully contracts, in order to assist the diastolic function.

Compressible elements 20 may be manufactured by using conventional spring manufacturing techniques, wire curving processes which may be followed by a suitable thermal treatment to set mechanical characteristics and relax curving tensions. Compressible elements 20 may be manufactured from a type of elastic metal or plastic material, such as but not limited to, Nitinol, stainless steel, silicon, or a suitable alloy, composite compound, or absorvable material, preferably from an absorvable material (e.g., PLLA, PGA, or PLA). Most preferably, compressible elements 20 are made from a wire, having thickness of about 0.45 mm, turned in a shape of a spring. The length of compressible elements 20 may generally be in the range of 2 to 15 mm, preferably about 10 mm.

Figure 14:
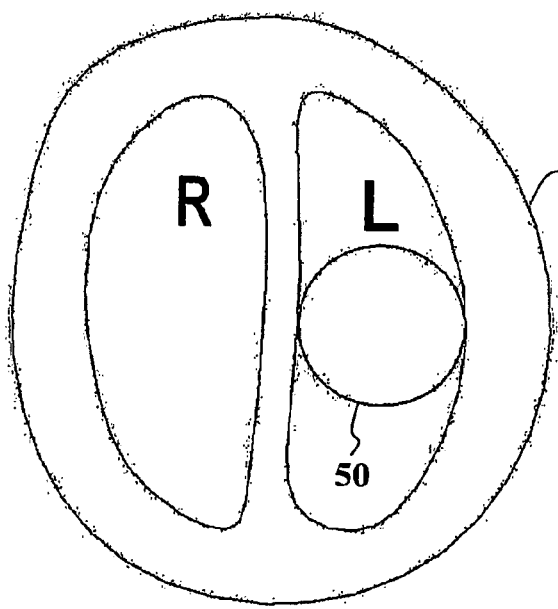
FIG. 14 illustrates a device for treating ventricular dysfunctions by means of an inflatable balloon.

FIG. 14 illustrates another preferred embodiment in which an expandable balloon 50 is used for expanding the left ventricle of the heart 10. This procedure may be used for example for mechanically expanding the left ventricle in order to 'break' intercellular connections and extracellular tissue of the ventricle, in order to reduce its rigidity and stiffness. This treatment may be advantageously used, for example, before mounting the elastic and attachment elements on the wall of the heart, or independently, as a standalone treatment, or in combination with other treatments. Balloon 50 may be a conventional balloon of a balloon catheter, which may be introduced into the heart 10 using conventional procedures, as well known to those skilled in the art. The diameter of inflatable balloon 50 should be configured according to the dimensions of the treated ventricle, for example, in the case of adult patients the diameter of fully inflated inflatable balloon 50 is typically about 50±20 mm.

The elastic elements (13a, 13b, 13c and/or 13d), attachment elements (7, 8, 15a, 45 and/or 55), gripping tools (60, 70, 80 and/or 90), distance indicating instruments (100, 101, 102, 103, 104 and/or 105), and/or compressible elements (20) and expandable balloons (50), or modifications/variations thereof, may assemble a kit to be used by surgeons in heart treatment surgery. A typical procedure for mounting a ventricular assisting system of the invention may include the following steps:

a) performing a chest incision, such as, but not limited to, thoracotomy/MIS (minimal invasive surgery—in cases wherein smaller incisions or keyhole surgery is in preference);
b) attaching an attachment element (e.g., 7, 8, 15*a*, 45 or 55), preferably by means of a gripping tool (e.g., 60, 70, 80 and/or 90), by puncturing and advancing/threading said attachment element into the wall of the heart and removing said gripping tool when tissue resistance is encountered;
c) determining the distance to a location for a new attachment element to be attached, preferably by means of a distance indicating instruments (100, 101, 102, 103, 104 or 105);
d) attaching said new attachment element to the wall of the heart at the location determined above, preferably by means of a gripping tool, as described in step b);
e) attaching an elastic element (13*a*, 13*b*, 13*c* and/or 13*d*) to the attachment elements; (Optionally by gripping tool);
f) repeating steps c) to e) to form a chain of an alternating series of said elastic elements and said attachment elements.

An additional such chain of alternating series of elastic elements and attachment elements may be mounted on the wall of the heart, preferably in parallel, by determining a distance from a previously installed chain of said elastic elements and attachment elements, preferably by means of a distance indicating instrument, and mounting said additional chain within said distance, by carrying out steps b) to f).

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different loops, rings, cylindrical and shaft elements, and other members, described hereinabove may be constructed in different shapes (e.g. having oval, square etc. form in plan view) and sizes from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A system that improves diastolic function of the heart comprising:
a) Elastic elements, each of which comprise one or more torsion springs, each torsion spring further comprising one or more torsion loops at the apex and two arms forming a "V" or "U" like shape radiating from the apex; and
b) Attachment elements;
wherein the extremities of the elastic elements are bent to form curved fasteners that anchor the elastic elements to an anchoring means of the attachment elements wherein said elastic elements and said attachment elements interconnect to form a chain formed of an alternating series of said elastic elements and said attachment elements; and
wherein said attachment elements are adapted to be anchored in the wall of the heart and with option for drug delivery to the wall of the heart.

2. The system according to claim 1, wherein the elastic elements comprise a single torsion spring and two arms forming a "V"-like shape, wherein each of the arms comprises a curved fastener shaped in a form of a spiral, or a "G"-like shape.

3. The system according to claim 2, wherein the end portion of each arm is curved into an "S"-like shape, wherein the bottom part of said "S"-like shape is further curved to provide the spiral, or a "G"-like shape curved fastener.

4. The system according to claim 1, wherein each elastic element is comprised of a relatively straight arm and an arm having a curved section relative to the plane of the torsion spring and the relatively straight arm of said elastic element.

5. The system according to claim 1, wherein at least one of the curved fasteners of the elastic elements comprises one or more fastening loops configured to be placed and tightened over a portion of an anchoring element.

6. The system according to claim 5, wherein the other curved fastener of the elastic elements is provided in a form of an anchoring loop.

7. The system according to claim 5, further comprising a widening loop provided on, or near, the fastening loops for assisting in widening the fastening loops before placing them over a portion of the anchoring element.

8. The system according to claim 5, further comprising a saddle formed on an arm section of the elastic element near the curved fastener for assisting in widening the fastening loops.

9. The system according to claim 1, wherein the elastic elements are comprised of two "V"-shaped torsion springs having a mutual arm, which form a zigzagged shape element, wherein the non-mutual arms comprise curved fasteners.

10. The system according to claim 1, wherein the attachment elements are formed in a shape of a helix having an attachment section and a head section, wherein the attachment section is configured to be threaded into a tissue and the head section comprises the anchoring means for anchoring component.

11. The system according to claim 10, wherein the attachment elements further comprise a neck section, provided between the attachment section and the head section, said neck section is configured to prevent excess threading of the attachment element into the tissue.

12. The system according to claim 11, wherein the neck section is formed by abruptly reducing the distances between the helix loops above the attachment section of the attachment element.

13. The system according to claim 11, wherein the anchoring means for anchoring the elastic elements to the attachment elements, of said attachment elements are a continuation of the neck section which helix loops are having a slightly reduced radius.

14. The system according to claim 1, wherein the anchoring means for anchoring the elastic elements to the attachment elements, are implemented as anchoring loops provided in the attachment element.

15. The system according to claim 1, wherein the attachment elements are intramural anchors having one or more barbs attached to a nail section of the intramural anchor.

16. The system according to claim 1, further comprising an elastic wire or stretchable cord mounted over the outer wall of the heart by means of attachment elements.

17. The system according to claim 1, further comprising an elastic wire or stretchable cord configured to be connected to the attachment elements at the extremities of the chain formed of the alternating series of the elastic elements and the attachment elements, wherein said elastic wire or stretchable cord and said chain of elastic elements and attachment elements encircles a perimeter of the heart.

18. The system according to claim 1, further comprising an inflatable balloon configured to be introduced into a ventricle of the heart and being inflated thereinside.

19. The system according to claim 1, further comprising one or more compressible elements configured to be threaded into the wall of the heart.

20. A device that improves diastolic function of the heart comprising an elastic element comprising one or more torsion springs, each torsion spring further comprising one or more torsion loops at the apex and two arms forming a "V" or "U" like shape radiating from the apex, wherein the extremities of said elastic element are bent to form curved fasteners that anchor the elastic elements to an anchoring loop or ring, and wherein said anchoring loop or ring is adapted to be anchored in the wall of the heart.

21. A method for improving diastolic function of the heart, comprising:
 a) Performing a chest incision;
 b) Attaching an attachment element to the wall of the heart, said attachment element-is capable of puncturing the heart tissue and being advanced or threaded thereinto;
 c) Determining the distance from a previously attached attachment element to a location for a new such attachment element to be attached to the wall of the heart;
 d) Attaching said new attachment element to the wall of the heart at said location;
 e) Attaching an elastic element comprising a torsion spring, each torsion spring further comprising one or more torsion loops at the apex and two arms forming a "V" or "U" like shape radiating from the apex, to anchoring means provided in said previously attached attachment element and said new attachment element by means of curved fasteners provided in the extremities of said arms of said torsion spring, such that one arm extremity is attached to the anchoring means provided in said previously attached attachment element and the other arm extremity is attached to the anchoring means provided in said new attachment element;
 f) Repeating steps c) to e) to form a chain of an alternating series of said elastic elements and said attachment elements.

22. The method according to claim 21, wherein the attachment elements are attached by means of a gripping tool, comprising:
 a) Gripping the anchoring means of an attachment element by said gripping tool;
 b) Puncturing the wall of the heart with a sharp tip of said attachment element and advancing/threading said attachment element thereinto until tissue resistance is encountered; and
 c) Removing said gripping tool.

23. A method according to claim 21, wherein the distance from the previously mounted attachment element is determined by means of a distance indicating instrument having one or more arms having suitable lengths.

24. A method according to claim 21, comprising mounting additional one or more such chains of alternating series of elastic elements and attachment elements on the wall of the heart, comprising:
 i) Determining a distance from a previously installed chain of said elastic elements and said attachment elements; and
 ii) Mounting an additional chain of alternating series of elastic elements and attachment elements on the wall of the heart within said distance, by carrying out steps b) to f) of claim 21.

25. A method according to claim 24, wherein the distance from the previously installed chain is determined by means of a distance indicating instrument having one or more arms having suitable lengths.

26. A method according to claim 24, wherein the one or more chains of alternating series of elastic elements and attachment elements are substantially parallel.

27. The method according to claim 21, further comprising attaching an elastic wire or stretchable cord to the attachment elements at the extremities of the chain formed of the alternating series of the elastic elements and the attachment elements, wherein said elastic wire or stretchable cord and said chain of elastic elements and attachment elements encircles a perimeter of the heart.

28. The method according to claim 21, further comprising introducing an inflatable balloon into a ventricle of the heart and inflating the same thereinside.

29. The method according to claim 21, further comprising threading one or more compressible elements into the wall of the heart.

30. The method according to claim 21, wherein the chest incision is a mini-left thoracotomy or small incisions performed according to the keyhole surgery approach.

31. The method according to claim 21 wherein the curved fasteners are selected from a group consisting of anchoring loops, fastening rings, "G"-shaped curved fasteners, "S"-like shaped curved fasteners, spiral shaped curved fasteners.

32. A kit of elements and instruments that are configured to mount a ventricular function assisting system on the wall of a heart, comprising: at least two attachment elements configured to attach to a wall of a heart, one or more elastic elements, each comprising a torsion spring, each torsion spring further comprising one or more torsion loops at the apex and two arms forming a "V" or "U" like shape radiating from the apex, that connect to anchoring means for anchoring the elastic elements to the attachment elements, wherein said anchoring means are provided in said attachment elements, a gripping tool that grips and holds said anchoring means, and one or more distance indicating instrument that indicates distances between adjacent attachment elements and/or the distances between interconnected chains of said attachment and elastic elements.

33. The kit according to claim 32, further comprising one or more compressible elements capable of being threaded into the wall of the heart, an expandable balloons configured to be introduced into a ventricle of the heart and inflated thereinside, and/or an elastic wire or stretchable cord capable of being connected to the anchoring means for anchoring the elastic elements to the attachment elements, wherein said anchoring means are provided in said attachment elements.

* * * * *